United States Patent
Duggal et al.

(10) Patent No.: US 9,125,754 B2
(45) Date of Patent: *Sep. 8, 2015

(54) ARTIFICIAL SPINAL DISC

(75) Inventors: Neil Duggal, London (CA); Louise Raymond, London (CA); Daniel R. Baker, Seattle, WA (US); Robert Conta, Mercer Island, WA (US); Carly A. Thaler, Seattle, WA (US); David T. Stinson, Woodinville, WA (US)

(73) Assignee: SYNERGY DISC REPLACEMENT, INC., Kitchener (CA)

( * ) Notice: Subject to any disclaimer, the term of this patent is extended or adjusted under 35 U.S.C. 154(b) by 1082 days.

This patent is subject to a terminal disclaimer.

(21) Appl. No.: 12/241,344

(22) Filed: Sep. 30, 2008

(65) Prior Publication Data

US 2009/0043393 A1 Feb. 12, 2009

Related U.S. Application Data

(63) Continuation of application No. 10/590,139, filed as application No. PCT/US2005/023134 on Jun. 30, 2005, now Pat. No. 8,100,974.

(60) Provisional application No. 60/584,240, filed on Jun. 30, 2004, provisional application No. 60/658,161, filed on Mar. 4, 2005.

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/4657* (2013.01); *A61F 2/4684* (2013.01); *A61F 2/4611* (2013.01); *A61F 2002/302* (2013.01); *A61F 2002/305* (2013.01); *A61F 2002/3039* (2013.01); *A61F 2002/3065* (2013.01); *A61F 2002/3069* (2013.01); *A61F 2002/30232* (2013.01); *A61F 2002/30242* (2013.01); *A61F 2002/30354* (2013.01); *A61F 2002/30364* (2013.01); *A61F 2002/30369* (2013.01); *A61F 2002/30383* (2013.01); *A61F 2002/30397* (2013.01); *A61F 2002/30426* (2013.01); *A61F 2002/30535* (2013.01); *A61F 2002/30538* (2013.01);

(Continued)

(58) Field of Classification Search
CPC  A61F 2/44; A61F 2002/443; A61F 2002/444
USPC ........................................... 623/17.11–17.16
See application file for complete search history.

(56) References Cited

U.S. PATENT DOCUMENTS

| | | |
|---|---|---|
| 3,867,728 A | 2/1975 | Stubstad |
| 3,875,595 A | 4/1975 | Froning |
| 4,309,777 A | 1/1982 | Patil |
| 4,714,469 A | 12/1987 | Kenna |
| 4,863,476 A | 9/1989 | Shepperd |
| 4,863,477 A | 9/1989 | Monson |

(Continued)

FOREIGN PATENT DOCUMENTS

| | | |
|---|---|---|
| DE | EP176728 A1 | 4/1986 |
| DE | EP298233 A1 | 1/1989 |

(Continued)

*Primary Examiner* — Bruce E Snow
(74) *Attorney, Agent, or Firm* — Maywood IP Law; Barbara Daniels; David Meibos

(57) ABSTRACT

An artificial disc prosthesis is provided. The prosthesis of the present invention enables spinal segment alignment by having a variable height across its surface. The variable height is achieved by an asymmetric artificial nucleus or by at least one variable height end plate.

30 Claims, 19 Drawing Sheets

(52) U.S. Cl.
CPC ............... *A61F2002/30563* (2013.01); *A61F 2002/30578* (2013.01); *A61F 2002/30604* (2013.01); *A61F 2002/30616* (2013.01); *A61F 2002/30654* (2013.01); *A61F 2002/30662* (2013.01); *A61F 2002/30663* (2013.01); *A61F 2002/30685* (2013.01); *A61F 2002/30841* (2013.01); *A61F 2002/30884* (2013.01); *A61F 2002/30892* (2013.01); *A61F 2002/30904* (2013.01); *A61F 2002/443* (2013.01); *A61F 2220/0025* (2013.01); *A61F 2220/0033* (2013.01); *A61F 2230/0065* (2013.01); *A61F 2230/0069* (2013.01); *A61F 2230/0071* (2013.01); *A61F 2250/0006* (2013.01); *A61F 2250/0058* (2013.01); *A61F 2310/00017* (2013.01); *A61F 2310/00023* (2013.01); *A61F 2310/00029* (2013.01); *A61F 2310/00179* (2013.01); *A61F 2310/00407* (2013.01); *A61F 2310/00796* (2013.01)

(56) References Cited

U.S. PATENT DOCUMENTS

| | | | |
|---|---|---|---|
| 4,874,389 A | 10/1989 | Downey | |
| 4,911,718 A | 3/1990 | Lee | |
| 4,946,378 A | 8/1990 | Hirayama | |
| 4,997,432 A | 3/1991 | Keller | |
| 5,002,576 A | 3/1991 | Fuhrmann | |
| 5,071,437 A | 12/1991 | Steffee | |
| 5,123,926 A | 6/1992 | Pisharodi | |
| 5,258,031 A | 11/1993 | Salib | |
| 5,306,308 A | 4/1994 | Gross | |
| 5,314,477 A | 5/1994 | Marnay | |
| 5,320,644 A * | 6/1994 | Baumgartner | 623/17.16 |
| 5,350,644 A | 9/1994 | Graetzel | |
| 5,370,697 A | 12/1994 | Baumgartner | |
| 5,401,269 A | 3/1995 | Buttner-Janz | |
| 5,458,642 A | 10/1995 | Beer | |
| 5,507,816 A | 4/1996 | Bullivant | |
| 5,534,029 A | 7/1996 | Shima | |
| 5,534,030 A | 7/1996 | Navarro | |
| 5,556,431 A | 9/1996 | Buttner-Janz | |
| 5,645,596 A | 7/1997 | Kim | |
| 5,674,294 A | 10/1997 | Bainville | |
| 5,676,701 A | 10/1997 | Yuan | |
| 5,676,702 A | 10/1997 | Ratron | |
| 5,683,465 A | 11/1997 | Shinn | |
| 5,702,450 A | 12/1997 | Bisserie | |
| 5,755,796 A | 5/1998 | Ibo | |
| 5,824,094 A | 10/1998 | Serhan | |
| 5,827,328 A | 10/1998 | Buttermann | |
| 5,865,846 A | 2/1999 | Bryan | |
| 5,888,226 A * | 3/1999 | Rogozinski | 623/17.16 |
| 5,893,889 A | 4/1999 | Harrington | |
| 5,895,428 A | 4/1999 | Berry | |
| 5,898,428 A | 4/1999 | Zimlich | |
| 5,899,941 A | 5/1999 | Nishijima | |
| 5,919,235 A | 7/1999 | Husson | |
| 5,928,284 A | 7/1999 | Mehdizadeh | |
| 5,989,291 A | 11/1999 | Ralph | |
| 6,001,130 A | 12/1999 | Bryan | |
| 6,019,792 A | 2/2000 | Cauthen | |
| 6,039,763 A | 3/2000 | Shelokov | |
| 6,051,751 A | 4/2000 | Sioshansi | |
| 6,063,121 A | 5/2000 | Xavier | |
| 6,066,174 A | 5/2000 | Farris | |
| 6,113,637 A | 9/2000 | Gill | |
| 6,136,031 A | 10/2000 | Middleton | |
| 6,146,421 A | 11/2000 | Gordon | |
| 6,146,422 A | 11/2000 | Lawson | |
| 6,179,874 B1 | 1/2001 | Cauthen | |
| 6,368,350 B1 | 4/2002 | Erickson | |
| 6,375,682 B1 | 4/2002 | Fleischmann | |
| 6,402,785 B1 | 6/2002 | Zdeblick | |
| 6,416,551 B1 | 7/2002 | Keller | |
| 6,468,310 B1 | 10/2002 | Ralph | |
| 6,478,800 B1 | 11/2002 | Fraser | |
| 6,517,580 B1 | 2/2003 | Ramadan | |
| 6,520,996 B1 | 2/2003 | Manasas | |
| 6,527,804 B1 | 3/2003 | Gauchet | |
| 6,562,045 B2 | 5/2003 | Gil | |
| 6,579,320 B1 | 6/2003 | Gauchet | |
| 6,579,321 B1 | 6/2003 | Gordon | |
| 6,592,624 B1 | 7/2003 | Fraser | |
| 6,599,320 B1 | 7/2003 | Kuslich | |
| 6,610,093 B1 | 8/2003 | Pisharodi | |
| 6,626,943 B2 | 9/2003 | Eberlein | |
| 6,652,533 B2 | 11/2003 | O'Neil | |
| 6,669,730 B2 | 12/2003 | Ralph | |
| 6,682,562 B2 | 1/2004 | Viart | |
| 6,706,068 B2 | 3/2004 | Ferree | |
| 6,709,439 B2 | 3/2004 | Rogers | |
| 6,726,720 B2 | 4/2004 | Ross | |
| 6,740,118 B2 | 5/2004 | Eisermann | |
| 6,749,635 B1 | 6/2004 | Bryan | |
| 6,761,723 B2 | 7/2004 | Buttermann | |
| 6,770,094 B2 | 8/2004 | Fehling | |
| 6,770,095 B2 | 8/2004 | Grinberg | |
| 6,793,678 B2 | 9/2004 | Hawkins | |
| 6,881,228 B2 | 4/2005 | Zdeblick | |
| 6,899,735 B2 | 5/2005 | Coates | |
| 6,908,484 B2 | 6/2005 | Zubok | |
| 6,936,071 B1 | 8/2005 | Marnay | |
| 6,949,105 B2 | 9/2005 | Bryan | |
| 6,960,232 B2 | 11/2005 | Lyons | |
| 6,964,686 B2 | 11/2005 | Gordon | |
| 6,966,929 B2 | 11/2005 | Mitchell | |
| 6,976,988 B2 | 12/2005 | Ralph | |
| 6,986,789 B2 | 1/2006 | Schultz | |
| 6,989,032 B2 | 1/2006 | Errico | |
| 6,994,727 B2 | 2/2006 | Khandkar | |
| 7,001,432 B2 | 2/2006 | Keller | |
| 7,001,433 B2 | 2/2006 | Songer | |
| 7,025,787 B2 | 4/2006 | Bryan | |
| 7,048,764 B2 | 5/2006 | Ferree | |
| 7,048,766 B2 | 5/2006 | Ferree | |
| 7,056,344 B2 | 6/2006 | Huppert | |
| 7,060,097 B2 | 6/2006 | Fraser | |
| 7,060,099 B2 | 6/2006 | Carli | |
| 7,066,961 B2 | 6/2006 | Michelson | |
| 7,101,400 B2 | 9/2006 | Thramann | |
| 7,105,024 B2 | 9/2006 | Richelsoph | |
| 7,118,580 B1 | 10/2006 | Beyersdorff | |
| 7,147,665 B1 | 12/2006 | Bryan | |
| 7,153,325 B2 | 12/2006 | Kim | |
| 7,156,848 B2 | 1/2007 | Ferree | |
| 7,156,876 B2 | 1/2007 | Moumene | |
| 7,166,131 B2 | 1/2007 | Studer | |
| 7,179,294 B2 | 2/2007 | Eisermann | |
| 7,201,776 B2 | 4/2007 | Ferree | |
| 7,204,852 B2 | 4/2007 | Marnay | |
| 7,217,291 B2 | 5/2007 | Zucherman | |
| 7,226,452 B2 | 6/2007 | Zubok | |
| 7,235,101 B2 | 6/2007 | Berry | |
| 7,244,275 B2 | 7/2007 | Michelson | |
| 7,250,060 B2 * | 7/2007 | Trieu | 623/17.15 |
| 7,255,714 B2 | 8/2007 | Malek | |
| 7,267,691 B2 | 9/2007 | Keller | |
| 7,276,082 B2 | 10/2007 | Zdeblick | |
| 7,291,171 B2 | 11/2007 | Ferree | |
| 7,364,589 B2 | 4/2008 | Eisermann | |
| 8,100,974 B2 * | 1/2012 | Duggal et al. | 623/17.15 |
| 8,172,904 B2 * | 5/2012 | Duggal et al. | 623/17.15 |
| 2002/0035400 A1 | 3/2002 | Bryan | |
| 2004/0002761 A1 * | 1/2004 | Rogers et al. | 623/17.13 |
| 2004/0153157 A1 | 8/2004 | Keller | |
| 2004/0158328 A1 | 8/2004 | Eisermann | |
| 2004/0243240 A1 | 12/2004 | Beaurain | |
| 2005/0015152 A1 | 1/2005 | Sweeney | |
| 2005/0113926 A1 | 5/2005 | Zucherman | |
| 2005/0159818 A1 | 7/2005 | Blain | |
| 2005/0216086 A1 | 9/2005 | Marik | |
| 2006/0030862 A1 | 2/2006 | De Villiers | |

(56) References Cited

U.S. PATENT DOCUMENTS

| | | |
|---|---|---|
| 2006/0052872 A1 | 3/2006 | Studer |
| 2006/0116768 A1 | 6/2006 | Krueger |
| 2006/0136061 A1 | 6/2006 | Navarro |
| 2007/0198093 A1 | 8/2007 | Brodke |
| 2007/0225812 A1 | 9/2007 | Gill |
| 2009/0216330 A1 | 8/2009 | Geisert |

FOREIGN PATENT DOCUMENTS

| | | |
|---|---|---|
| EP | 042271 A1 | 12/1981 |
| EP | 282161 A1 | 9/1988 |
| FR | 2730159 | 8/1996 |
| FR | 2805985 | 9/2001 |
| RU | 2080841 | 6/1997 |
| WO | WO9526697 A1 | 10/1995 |
| WO | WO 2004041131 | 5/2004 |
| WO | WO2004064692 A2 | 8/2004 |
| WO | WO2004089259 A1 | 10/2004 |
| WO | WO2005039455 A1 | 5/2005 |
| WO | WO2005046534 A1 | 5/2005 |
| WO | WO2005053580 A1 | 6/2005 |
| WO | WO2007063398 A2 | 6/2007 |

* cited by examiner

ARTIFICIAL SPINAL DISC

CROSS-REFERENCE TO RELATED APPLICATIONS

This application is a continuation of:
pending prior U.S. patent application Ser. No. 10/590,139 and entitled ARTIFICIAL SPINAL DISC filed as a U.S. national stage filing of:
PCT Application No. PCT/US05/023134, filed Jun. 30, 2005 and entitled ARTIFICIAL SPINAL DISC, which claims the benefit of:
prior U.S. Provisional Patent Application Ser. No. 60/658,161, filed Mar. 4, 2005 and entitled ARTIFICIAL SPINAL DISC, and
prior U.S. Provisional Patent Application Ser. No. 60/584,240, filed Jun. 30, 2004 and entitled ARTIFICIAL DISK FOR DEFORMITY CORRECTION.
The above-identified documents are hereby incorporated herein by reference.

TECHNICAL FIELD

The present invention relates to methods and devices for the treatment of disc disease and spinal deformities with an artificial disc replacement.

BACKGROUND OF THE INVENTION

Spinal arthroplasty is an emerging field that offers the promise of restoring and/or maintaining normal spinal motion. The goal of spinal arthroplasty is to reduce or eliminate adjacent segment disease (ASD) by maintaining the normal spinal biomechanics at the operative level. To accomplish this, an artificial cervical prosthesis must duplicate as closely as possible the natural spinal biomechanics, including maintaining the axial height of the disc as well as applying angular adjustment throughout the full range of motion of the natural spine.

The spine plays an integral role in neural protection, load bearing and motion. The vertebral column provides a strong, yet mobile central axis for the skeleton and is composed of twenty-four vertebral bodies with seventy-five stable articulations. The intervertebral disc is a fundamental component of the spinal motion segment, providing cushioning and flexibility. Adjacent vertebrae are linked together by three articulations: a) the vertebral bodies and disc, which transmit compressive and shear loads and provide flexibility, and b) by two facet joints, which protect the disc from translational shear stress and limit rotation. This "triple joint complex" allows for flexion, extension, lateral bending and rotation of the spine.

The intervertebral disc is composed of an inner gel-like matrix called the nucleus pulposus and an outer surrounding fibrous band called the annulus fibrosus. When compressive loads are placed on the spine, increased pressure in the nucleus pulposus is transmitted to the annulus, which bulges outwards. The degenerative cascade of the intervertebral disc initially involves desiccation of the nucleus pulposus. With decreased elasticity and dampening from the nucleus, increased loads are transmitted to the annulus and facets. The increased stress on the annulus can lead to fissures and radial tears in its collagen fibers. With further degeneration, this can lead to circumferential bulging of the disc, contained and uncontained disc herniations, and complete desiccation of the disc. This degenerative cascade can result in axial pain, by stimulating pain fibers in the annulus, or compression of spinal nerve roots and/or the spinal cord. This can manifest itself in motor weakness, pain and/or numbness in the arms or legs or both.

The structure and function of the discs may be altered by a variety of factors including repeated stress, trauma, infection, neoplasm, deformity, segmental instability and inflammatory conditions. Degeneration of the intervertebral disc is the most common etiology of clinical symptoms referable to the spine. Degeneration of the spine is a universal concomitant of human aging. In the cervical spine, neck and arm pain caused by nerve root compression has been estimated to affect 51% of the adult population. Spondylosis of the spine and aging are intimately related, with spondylosis increasing in both prevalence and severity with age. Fortunately, the majority of patients will improve without surgery. In approximately 10-15% of cases, spondylosis is associated with persistent nerve root and spinal cord compression and/or spinal pain, with a small percentage ultimately requiring surgery.

The most common type of surgery used in the United States for the treatment of degenerative disorders of the spine (spondylosis) is spinal fusion. In an interbody fusion, the diseased disc is removed and either a wedge of bone from the patient's hip, allograft or a metallic spacer is placed between the vertebrae where the disc was removed. This immobilizes the functional spinal unit. While this surgery has been successful in eliminating motion, there are disadvantages associated with it. By converting a mobile, functional spinal unit into a fixed, nonfunctional one, fusion results in increased strain patterns at levels adjacent to the fused segment. When a segment of the spine is fused, there is elimination of motion at the level of surgery. Therefore, the stresses that would normally be absorbed by the disc at the site of surgery are now transferred to adjacent segments. This can cause adjacent segment disease (ASD) to one or several spinal units adjacent to the affected level. ASD can be defined as a clinical syndrome of symptomatic degenerative changes occurring adjacent to a previously fused motion segment. Retrospective studies have estimated that ASD can occur in the cervical spine at a rate as high as 2.9% per year with a projected survivorship rate of 26% at 10 years (Hilibrand A S, Carlson G D, Palumbo M, Jones P K, Bohlman H H: Radiculopathy and myelopathy at segments adjacent to the site of a previous anterior cervical arthrodesis. J Bone Joint Surg (Am) 81:519-528, 1999).

In the cervical spine, thousands of North Americans undergo surgery for cervical spondylosis each year. The majority of these procedures involve an anterior discectomy with decompression of the spinal cord and/or nerve root. The primary indication for surgery in the management of cervical spondylosis is radiculopathy, myelopathy and/or neck pain. Following the discectomy, an anterior interbody fusion is commonly performed. Autologous bone harvested from the iliac crest or cadaveric bone is most commonly used to fill the space created by the removal of the disc. A number of other solutions have been suggested, including metallic devices such as fusion cages or other types of spacers, xenografts such as bovine bone, and biological strategies such as the use of growth factors. The graft for the interbody fusion can be shaped to correct underlying deformity of the cervical spine. By contouring the graft one can restore lordosis to a straight or kyphotic spine.

A more recent alternative to spinal fusion is replacement of the damaged disc with a motion preservation device, which includes either a nucleus or total disc replacement (TDR). The rationale for the development of the artificial disc is to prevent adjacent segment disease. Artificial disc devices can be broadly divided into two categories, those that replace the nucleus only, leaving the annulus and vertebral body end plates intact and those that involve replacement of the disc and addition of prosthetic end plates. Both strategies are directed at restoration of intervertebral disc function. Prosthetic nuclei are described, for example, in U.S. Pat. Nos. 5,047,055 and 5,192,326. United States Patent application US2002/0183848 also discloses a prosthetic spinal disc nucleus that has a hydrogel core surrounded by a constraining jacket.

There are several different types of prosthetic devices for use in the cervical or lumbar segments of the spine designed for TDR. For example, the Prodisc™ and the Charite™ disc are composites of cobalt chromium end plates with a polyethylene core. The Prodisc™ is described in U.S. Pat. No. 5,314,477 and the Charite™ disc is described in U.S. Pat. Nos. 5,401,269 and 5,556,431. The Prestige™ disc is another type of artificial disc that comprises a metal on metal design with a ball and trough articulation. Another type of artificial disc that is gaining popularity in the cervical spine is the Bryan® disc, described in several United States Patent applications including 2004/0098131; 2004/00544411; and 2002/0128715. The Bryan® disc is a composite artificial disc with a low friction, wear resistant, elastic nucleus that articulates with two circular metal plates.

Presently, there are at least four artificial cervical disc replacement systems undergoing clinical trials worldwide. These include unconstrained devices, such as the PCM cervical disc. These unconstrained devices do not have mechanical stops to limit their range of motion. The Bryan® Cervical disc, the Prodisc™ C and the Prestige™ LP cervical disc systems limit range of motion to varying degrees. These systems can be considered semi-constrained, in that there are mechanical stops outside the normal range of motion. Thus far, only the Charite™ disc has been approved for use in the United States.

Artificial spinal discs have been implanted for the management of degenerative disc disease producing radiculopathy, myelopathy and/or axial spinal pain. More recently, artificial discs have been adopted for the treatment of trauma. The aim of TDR is to reproduce the biomechanics of the natural disc. Early clinical and biomechanical studies with single and multi-level disc replacement have reported favorable clinical outcomes and preserved range of motion at the level of surgery. Preservation of range of motion, however, while an important feature of an artificial disc, is only a single measure of spinal biomechanics. The effect of the disc on angulation at the operative level, the average disc space height, and overall spinal alignment (sagittal and coronal balance) also needs to be considered.

While the introduction of artificial discs has led to many successful surgeries, there are still problems associated with the current discs. For example, all of the current artificial cervical discs have a fixed height across the entire disc. The artificial discs presently available can have issues with focal kyphosis or kyphosis at adjacent segments of the spine after the patient post-operatively reassumes an upright position, supporting the weight of the head and body. For instance, with the Bryan® disc, the end plates are allowed to move freely about all axes of rotation, allowing the end plate to assume a position resulting from the forces exerted on the implant by the head and neck. At times, this position may be significantly different from the positioning of the disc intra-operatively. Several published studies with the Bryan® cervical disc replacement system have reported a tendency for the end plates of the prosthesis and the alignment of the cervical spine to develop kyphosis following surgery. [Pickett G E, Mitsis D K, Sekhon L H et al. Effects of a cervical disc prosthesis on segmental and cervical spine alignment. *Neurosurg Focus* 2004; 17(E5):30-35; Johnson J P, Lauryssen C, Cambron H O, et al. Sagittal alignment and the Bryan® cervical disc. *Neurosurg Focus* 2004; 17(E14):1-4; Sekhon L H S. Cervical arthroplasty in the management of spondylotic myelopathy: 18 month results. *Neurosurg Focus* 2004; 17(E8):55-61.] This kyphotic angulation of the prosthesis has been attributed .to the passive (unconstrained motion with a mobile nucleus and variable instantaneous axis of rotation) design of the implant. None of the current TDR systems addresses this major complication.

A significant number of patients with spinal disc disease have a loss of sagittal alignment of the spine as a result of the degenerative process. In addition, varying degrees of coronal imbalance can also occur. None of the available artificial disc replacement systems are designed to restore normal alignment to a spine that is straight, which have focal/global kyphosis or coronal deformity. Existing artificial disc replacement systems that are inserted into either a straight, kyphotic or angulated segment are likely to take on the angle and local biomechanics determined by the facets, ligaments and muscle forces. As such, patients with a pre-operative straight spine may develop post-operative kyphosis, and patients with a pre-operative kyphosis may have a worsening of the deformity post-operatively. Kyphosis of the spine has been implicated in segmental instability and the development of clinically significant degenerative disease. Several clinical studies have described that a change in the sagittal or coronal balance of the spine can result in clinically significant axial spinal pain as well the initiation and/or the acceleration of ASD. [Kawakami M, Tamaki T, Yoshida M, et al. Axial symptoms and cervical alignment after anterior spinal fusion for patients with cervical myelopathy. *J Spinal Disord* 1999; 12:50-60; Harrison D D, Harrison D E, Janik T J, et al. Modeling of the sagittal cervical spine as a method to discriminate hypolordosis: results of elliptical and circular modeling in 72 asymptomatic subjects, 52 acute neck pain subjects, and 70 chronic neck pain subjects. Spine 2004; 29:2485-2492; Katsuura A, Hukuda S, Saruhashi Y, et al. Kyphotic malalignment after anterior cervical fusion is one of the factors promoting the degenerative process in adjacent intervertebral levels. Eur Spine J 2001; 10:320-324; Ferch R D, Shad A, Cadoux-Hudson T A, Teddy P J. Anterior correction of cervical kyphotic deformity: effects on myelopathy, neck pain, and sagittal alignment. J Neurosurg 2004; 100: S13-S19; Katsuura A, Hukuda S, Imanaka T, Miyamoto K, Kanemoto M. Anterior cervical plate used in degenerative disease can maintain cervical lordosis. *J Spinal Disord* 1996; 9:470-476.]

Attempting to provide a deformity correction by simply altering the end plate or the nucleus of an artificial disc, while still maintaining free movement about all axes of rotation, may not be sustainable as the forces exerted by the head and body on the artificial disc could counteract the desired correction. To provide a sustainable correction, some limitation on the axes of rotation is required. From a design perspective, the goal is to design an artificial disc that is able to correct deformity (coronal and sagittal), has mechanical stops outside the normal range of motion (semi-constrained), and preferably has variable instantaneous axis of rotation (IAR).

The limits on the axes of rotation can fall into two categories. One is to provide correction using a permanent rotation or translation of an axis to support the correction. This is accomplished using the geometries of the core and end plates themselves and is referred to the Geometric Constraint category. The second is to keep free range of motion about all axes but provide the correction using a material support. This type of design provides the correction by the imposition of a deformable material in the plane of correction for normal rotation in that plane. This is the Material Constraint category of designs.

Degenerative disc disease is a major source of morbidity in our society. It can lead to serious economic and emotional problems for those afflicted. Thus, there is a need for an artificial disc that can alleviate both symptoms and correct deformity (sagittal or coronal or both) of the spine.

BRIEF SUMMARY OF THE INVENTION

There are a number of different strategies that can be used with disc replacements to address the need for alignment/deformity correction in the spine. With most of the available discs, the angle of disc insertion can significantly alter the orientation of the prosthesis. This is related to bone removal and end-plate preparation for the prosthesis. By changing the angle of insertion, the disc can be placed either in parallel or at an angle to the disc space. Unfortunately, by changing only the angle of insertion, one cannot correct an underlying deformity of the spine. Simply changing the angle of insertion is not adequate to compensate for a device that does not have sufficient off-center load bearing support or structure to maintain the correction of the deformity.

A strategy to correct lordosis in the lumbar spine has been utilized by the Link-Charite™ and Prodisc™ lumbar disc replacement systems by using wedge-shaped end plates. A wedge-shaped end plate has also been used in at least one case with the Bryan™ cervical disc system. However, wedge-shaped end plates are not routinely available at the present time for cervical disc replacement systems. The strategy of using wedge-shaped end plate(s) involves forming a differential thickness across the end plate. The articulation between the ball and socket/trough or the nucleus and end plates is not altered, which is an advantage because the complex geometry of how the prosthesis provides motion is not altered. The disadvantage, however, is that this strategy is not forgiving if an error is made with either an overly corrected end plate or an end plate that is not corrected enough. The revision of the end plate can be difficult at the time of surgery and may even preclude the disc space from receiving a disc replacement. As most systems have a coating on the end plates that promote bony ingrowth, revision at a later date may be extremely difficult or even impossible. As there are two surfaces to the end plate, an outer surface that contacts the bone and an inner surface that articulates with the nucleus or core, it is conceivable that by changing the location or geometry of the inner surface, one could alter the center of rotation. This would be most applicable to prostheses that function as a "ball and socket" articulation. By changing the location of the "socket" or trough, this could alter how the prosthesis impacts alignment at the level of the disc.

An alternate method of achieving lordotic correction is by changing the nucleus or inner core. The biggest advantage of this approach is that the nucleus or core can be more easily interchanged or revised. Intra-operatively, instruments can be used to gage the need for and amount of correction and the appropriate nucleus can be inserted. By designing the correction into the nucleus, the surgeon is provided with flexibility and ease of insertion, and the ability for revision at a later date, which the other methods do not provide.

The invention includes a novel artificial disc that provides the normal range of motion of the natural intervertebral disc, along with the ability to correct deformity of the spine. The proposed disc allows for semi-constrained range of motion of the functional spinal unit. It will reproduce the kinematics of the pre-operative normal spine. It will possess maximum durability and biocompatibility, and a means for integrating itself into the spine bony structure for long-term stability. Its insertion will be safe, simple, and ideally not add significantly to surgical time compared with the current procedures. In contrast to the existing disc replacement systems, it will allow the surgeon to correct deformity while maintaining natural kinematics of the spine.

A major advantage of this system will be that the nucleus may be easily revisable. For instance, in most cases where the Bryan® disc needs revision, the entire disc, including the end plates, must be removed. In cases where the alignment of the spine changes with time, especially in children and young adults, this new disc replacement system will allow revision of the nucleus, if needed.

The present invention addresses the problems associated with the artificial discs of the prior art by providing an artificial disc that provides for correction of spinal alignment deformity.

The artificial disc of the present invention is useful for the treatment of degenerative disc disease including correcting spinal deformities such as kyphosis, lordosis, and scoliosis.

It is an object of one aspect of the invention to provide an improved artificial disc replacement that maintains motion at the operative level and reduces the incidence of adjacent segment disease.

In one aspect of the invention, the artificial disc incorporates an artificial nucleus having an asymmetrical maximum vertical axis. The present invention includes a non-spherical nucleus with a maximum point of load-bearing and height in a non-central location (a differential in the anterior/posterior height of the nucleus).

In one embodiment, the nucleus is adapted to provide lordodic correction to a damaged spinal segment. In this case, the axis of greatest height is positioned in the anterior part of the nucleus.

In another embodiment, the nucleus is adapted to provide kyphotic adjustment. In this case, the maximum height axis is positioned in the posterior part of the nucleus.

In yet another embodiment, the asymmetrical nucleus can be used for the treatment of scoliosis. To achieve this, the axis of maximum height is lateral (parasagittal) to the middle of the disc.

According to another aspect of the present invention, an artificial nucleus, or core, is provided for use in an artificial disc. The nucleus comprises a body of biocompatible material, having the greatest vertical height either at the central vertical axis or at a vertical axis other than the central vertical axis.

In another embodiment, the body is spherical or ovoid (egg-shaped), having convex upper and lower surfaces and a non-central maximum height vertical axis. In an alternative embodiment, the nucleus is in the form of a truncated cylinder where the top is cut at a plane that is not parallel to the base. In another preferred embodiment, the disc is essentially circular.

It has been found that nucleus body designs with a completely rounded surface (not necessarily spherical) have issues with reliably maintaining correction when exposed to the variable forces of the head and neck. To address this issue, a segment or section that is flat or which has a contour different from the adjacent surface, can be formed in the central region of the nucleus body. This section will be referred to as a flattened section, which is meant to refer to any contour that is not the same as the adjacent surface(s) of the nucleus. Such a flattened surface can be planar or it can have other shapes such as a slight convex or concave shape with a radius of curvature different from the adjacent surface. Such a flattened surface could also be in the shape of a compound curve or other complex shape. In the example of providing a lordotic correction, the flattened segment can be angled relative to the superior end plate of the inferior vertebral body with the height of the anterior part being greater than the height of the posterior part. The overall shape of the nucleus body is still asymmetric, but the flattened segment is incorporated to provide a reliable correction of the deformity. This flat segment provides stabilization of the correction by resisting misalignment moments acting through the nucleus. If the flattened segment is not of adequate size, there may be a tendency for the correction to disappear in the presence of an anterior load or for a hyper-lordotic over correction in the presence of a posterior load (during lordotic correction). An additional advantage of incorporating a flat segment in the nucleus is to provide surface contact over that area during small motions about the resting, neutral position of the device. This should help reduce wear on the device.

In another embodiment, the nucleus or core could be hemispherical in shape with a flattened inferior surface that fits in an opening or trough formed in the lower end plate. Alternatively, the nucleus is asymmetric in that it has a greater vertical dimension or thickness on the anterior aspect than on the posterior aspect in order to provide a lordotic correction. The superior surface of the nucleus can have a flattened portion. The flattened portion may incorporate a concave segment, but can have the other configurations as mentioned above. The shape of the trough can be such that it defines the outer limits of rotational or translational movement of the nucleus relative to the lower end plate. This design allows for greater ease of insertion of the nucleus without undue distraction of adjacent vertebrae because the trough could be open at one end to allow for the nucleus to be inserted, and then a stop could be inserted in the trough to maintain the nucleus in the trough.

In another embodiment, instead of ovoid shaped nucleus, an elongated or "sausage type" shape can be used, which has spherical or ovoid end sections and a flattened or cylindrical center section. When a nucleus of this shape mates with a cylindrical bearing surface on the upper end plate, both surface and line contact are provided during lateral bending as well as in flexion and extension. When this type of elongated nucleus is used, a corresponding end plate trough in the lower end plate can be provided that allows for axial rotation with stops beyond the limits of normal motion. This trough can have the shape of a "bow tie," "dog bone" or the like. The trough can be slightly oversized compared with the nucleus to allow limited anterior/posterior and medial/lateral translation. Additionally, the bearing surface of the end plate trough can be curved upwardly at the outer limits of movement of the nucleus. This feature forces the nucleus to rise upwardly when it rotates and cause an axial distraction of the device that forces the adjacent vertebral bodies apart and loads the tissues between them, resulting in a gradual stop to the motion. The translation of the core within the trough attempts to preserve the mobile instantaneous axis of rotation of the natural disc.

In another embodiment, an elongated or "sausage type" shape nucleus is shaped so that the superior surface of the nucleus possesses a depression or valley formed in the flattened section, which extends along the sagittal plane. This can be accomplished, for example, by removing material from the central region of the flattened segment of the nucleus, creating a valley between the side portions. The side portions are contiguous with the remaining elements of the nucleus, and do not protrude in the vertical plane. The side portions are preferably symmetrical about the sagittal plane.

Additionally, the trough can be open at the anterior end to allow for insertion of the nucleus without excessive distraction of the adjacent end plates. A locking mechanism can be provided to prevent the nucleus from being expelled from the trough after insertion of the nucleus.

In another aspect of the invention, a novel type of end plate is provided. Unlike other end plates, which require extensive preparation of the vertebral body surface, the present end plates have an essentially flat outer or vertebral-contacting surface that allows them to be easily inserted. In a preferred embodiment, the surface is a semi-round plate having at least one unidirectional keel for anchoring the plate in position. The outer surface of the end plate may be treated in a way that promotes bony ingrowth to enhance stability of the end plate in situ. In one embodiment, the outer (vertebral-contacting) surface and the inner (nucleus-contacting) surface are essentially parallel to each other. In another embodiment, the outer surface and the inner surface are non-parallel thereby giving the end plate an essentially wedge-like configuration. The orientation of the wide and narrow edges of the wedge can be adjusted to provide various types and degrees of spinal correction.

In another aspect of the invention the prosthesis comprises an artificial nucleus and at least one end plate. In this embodiment, the prosthesis comprises a superior end plate for attachment to an upper vertebral member, an inferior end plate for attachment to a lower vertebral member and a nucleus adapted to fit between the two end plates. The end plate of the invention has a generally flat surface on the bone contacting side and the appropriate geometric receptacle on the other side for articulating with the nucleus. A central keel can be formed in the center of the inner surface of the end plate to anchor the nucleus in position. The end plate can include a stop member to prevent the prosthesis from moving toward the spinal canal. The nucleus may also have a maximum vertical axis that is not at the geometric center.

In another embodiment, the nucleus has an upper surface with an upper receptacle and a lower surface with a lower receptacle. The superior end plate has a downwardly projecting protrusion or anchor that engages the upper receptacle and the inferior end plate has an upwardly extending protrusion or anchor that engages the lower receptacle. The prosthesis maintains an appropriate spatial relationship between adjoining vertebrae and also permits normal range of motion of the spine. This embodiment can also include a receptacle that comprises a groove open at one end. The anchor on the end plate can include a central keel, which slides into position in the groove to secure the nucleus.

Another embodiment of the invention operates like a universal joint and incorporates three anatomical axes of rotation, two of which provide for flexion/extension and lateral bending motion, while the other one provides for axial rotation. These axes of rotation are accomplished by the use of a pair of two cylinders that can rotate relative to each about a central post.

In another embodiment, one of the plates has a central post that engages the other plate, and an annular core positioned around the central post that is formed of a resilient material. The core can be asymmetrical and engage both plates to provide necessary deformity correction. The core can engage the end plates to provide the desired angle between the plates for deformity correction, with the central post engaging the other plate when the load exceeds a predetermined limit. Or, the post can engage the other plate with the core engaging the other plate to maintain the plates at the desired angle relative to each other when applied forces tend to change the relative angle of the plates. Alternatively, the core could be replaced by two or more discrete spacers for performing the same function.

In another aspect of the invention, the nucleus can utilize material deformation to accomplish the desired ranges of motion. The shape of the material can be used to provide a restoring force for deformity correction. In order to achieve these results, material can be removed from various parts of the core to change the modulus of elasticity of the core at selected locations, or material having variable elastic moduli could be used. In this way, different forces and motions can be provided though the design of the core.

The end plates can be provided with features that act as stops outside of the desired range of motion, which allow for anatomically-derived gradual stopping. This result can be achieved by forming one or more camming surfaces in or on one of the end plates and providing a co-operating member on the other end plate for engaging the camming surface. The camming surface has a gradual curve on its inner surface. During relative movement between the end plates, the camming surface is engaged by the cooperating member, which results in an axial distraction of the end plates and provides a soft tissue assist to prevent a hard stop. Alternatively for rotational movement, cooperating camming surfaces can be provided so that distraction will occur when one end plate rotates relative to the other one.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set fourth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

These and other features of the invention will become more apparent from the following description in which reference is made to the appended drawings wherein.

DETAILED DESCRIPTION OF THE PREFERRED EMBODIMENTS

Figure 1A:
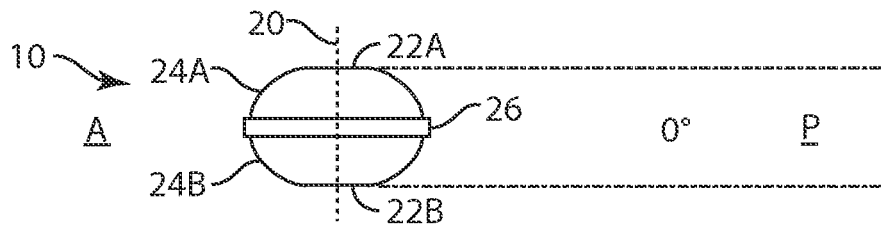
FIG. 1A illustrates an spherical artificial disc nucleus with the maximum central axis in the geometric midline of the nucleus.

The present invention relates to systems and methods for partially or wholly replacing diseased or injured joints with artificial joint prostheses. Those of skill in the art will recognize that the following description is merely illustrative of the principles of the invention, which may be applied in various ways to provide many different alternative embodiments.

This description is made for the purpose of illustrating the general principles of this invention and is not meant to limit the inventive concepts in the appended claims.

In its proper, healthy alignment, the spine follows natural curves, which promote proper sagittal and coronal balance (flexibility) and allow for balanced load sharing between the vertebrae. These curves include the cervical, thoracic, lumbar and sacral regions of the spine. Naturally, in order to accommodate a curve, there must be some variation in the angle of articulation between the functional spinal units and the height of an intradiscal space. The cervical and lumbar regions are naturally lordotic, or curved convexly in the anterior direction. At different segments along the spine, there are typically different heights for the vertebral bodies and the intradiscal space. In addition, the intradiscal space and vertebral body height may be different for different people.

Each intradiscal space has anterior and posterior regions. An artificial disc in the cervical, thoracic and lumbar regions that maintain the same height from the anterior to the posterior may promote an abnormal alignment, resulting in additional stress at the anterior or posterior portions of an adjacent disc. It may also result in an uneven load distribution across the device and cause an excessive amount of relative motion, wear debris and early failure.

As used herein, the terms, nucleus and core are used interchangeably to refer to an artificial intervertebral device that replaces a damaged natural spinal disc. The artificial core may be provided alone or in combination with a superior end plate for attachment to an upper vertebra or an inferior end plate for attachment to a lower vertebra or both.

The terms "upper" and "lower" are used herein to refer to the vertebrae on either side of the disc to be replaced, or a surface on a part in the position shown in the referenced drawing. A "superior" plate is affixed to an upper vertebra and an "inferior" plate is affixed to a lower vertebra of a functional spinal unit.

The terms vertical and horizontal are used herein relative to a standing human being in the anatomical position. The term "anterior" refers to the region towards the front and the term "posterior" refers to the region towards the back. The term "sagittal" refers to regions on either side of the central midline axis of a standing human being.

The term "asymmetrical" is used herein to refer to an axis of maximum height that is not placed centrally or to a nucleus or total disc replacement (TDR) not having its maximum vertical axis placed centrally. In other words, the maximum height is not situated or pivoted at a center line of symmetry so that the TDR comprises regions that are not exactly the same in shape or size as other regions on the other side of a line of symmetry. The location of maximal load bearing is located in a non-central location.

In one embodiment of the present invention, an artificial disc comprises a nucleus that is not geometrically symmetrical. The disc may have a maximum vertical axis that is not located at the geometric center of the disc. The maximum vertical axis may be located toward the front of the disc, the rear of the disc or on one side of the disc. The positioning of the maximum vertical height and load bearing capability is chosen depending on the type of deformity that needs to be corrected. The present invention also provides methods for the treatment of disc/vertebral body disease, lordosis, kyphosis and scoliosis using an asymmetric artificial disc.

One advantage of the present invention is that the "nucleus" or core may be interchanged and revised intraoperatively and post-operatively. Instruments can be used to gauge the need for and amount of correction and the appropriate implant can then be inserted. By introducing correction into the nucleus, the surgeon benefits from flexibility, ease of insertion and revisability that present systems do not provide.

Artificial discs of the present invention can be provided with various degrees of deformity correction. For this aspect of the invention, the surgeon can choose a disc having the appropriate correction for the patient. Thus, a method of treating a spinal deformity is provided. This method comprises preparing a spinal segment for implantation of an artificial disc, determining the desired angle of the intervertebral space, selecting an artificial nucleus having the desired dimensions, affixing a superior end plate to the upper vertebra, affixing an inferior end plate to the lower vertebra and inserting the selected nucleus between the superior and inferior end plates. Alternatively, and the assembled unit of end plate-nucleus-end plate may be inserted in unison. The configuration of the nucleus in this pre-assembled construct can be determined by the intra-operative measurement tools, or with pre-operative calculations. Pre-operative planning techniques and instruments may also be able to determine the size and orientation of this device for insertion.

A major advantage of the present system is that the artificial disc can be more easily and rapidly inserted and the nucleus can be changed or revised in accordance with the magnitude of the deformity being corrected. This is especially useful in children and young adults where the alignment of the spine changes over time.

In one embodiment, an asymmetric nucleus adapted for lordotic correction of the cervical spine is provided. The surgeon can restore lordosis to the cervical spine while maintaining motion. The nucleus may be composed of a low friction elastomer such as polyurethane, polycarbonate-polyurethane, a polymer such as polyethylene (particularly ultra-high molecular weight polyethylene), a suitable ceramic, metals or metal alloys such as titanium or a titanium alloy, chrome-cobalt-molybdenum (CoCrMo), cobalt 28 chromium molybdenum, cobalt chrome, stainless steel, or other suitable materials. It has a generally circular geometric design, with varying degrees of lordosis incorporated into it by utilizing an axis of maximum height anterior to the geometric center of the nucleus. The anterior height of the nucleus varies, depending on the extent of lordotic correction needed. The nucleus is available in various lordotic angles, e.g. 0, 3° and 6°, as well as differing heights (e.g., 4, 6 and 8 mm). Before deciding on the final nucleus size, a set of instruments or other means can be used to gauge the need for lordotic correction.

The nucleus slides between a superior end plate and an inferior end plate. The nucleus can be maintained in position using various types of connectors. For example, in one embodiment, the convex surface of the nucleus has a midline groove to allow the nucleus to slide into place between the positioned end plates. A central keel on the concave surface of the end plate is received in the groove of the nucleus. It is apparent that other types of connections can be used to maintain the nucleus in position. For example, a tooth and lock system or a pop-in system could be used.

A number of embodiments of the nucleus and artificial disc of the present invention are illustrated in the appended drawings. In one aspect of the invention, correction of spinal segment alignment is provided by an artificial nucleus which has the shape of a truncated cylinder or which is generally spherical or ovoid in shape, wherein the two halves on the arc on either side of a central axis are not symmetrical. In other words, the curvature is not geometrically parallel or symmetric.

In one embodiment, the implant consists of three pieces. The end plates will be made in differing sizes to accommodate differences in anatomy. These may be fabricated of titanium or a titanium alloy, chrome-cobalt-molybdenum (CoCrMo), cobalt 28 chromium molybdenum, cobalt chrome, stainless steel or other materials suitable for spinal prosthetic inserts.

The end plates can have two distinct surfaces. The flat surface of each end plate, which contacts the vertebral body end plate, is capable of accommodating bony ingrowth and incorporates a suitable coating, such as porous titanium, a calcium phosphate, or includes other types of known surfaces that promote bony ingrowth for long-term stability. The end plates can also have one or more parasagittal keels that provide immediate fixation. In one embodiment of the invention, a pair of parallel keels can be formed on the outer surface of one of the end plates, and a single, centrally-located keel can be formed on the outer surface of the other end plate. The other (inner) surface of the end plates can have a contour that corresponds with the geometric shape of the nucleus to form a bearing surface that allows for optimal articulation and wear characteristics with respect to the nucleus. In the middle of this bearing surface, there can be a single, central keel, which provides a constraint for the nucleus against excessive translation and range of motion. The nucleus can have a circular geometric design, with a midline groove to allow the nucleus to slide into place between the positioned end plates. A central keel on the concave surface of the end plate would fit into the groove of the nucleus. Before deciding on the final nucleus size, a set of instruments could be inserted to confirm the lordotic correction, but these may also be used as confirmation for other types of pre-surgical planning techniques and instrumentation. Alternatively, intra-operative instruments may be used as confirmation for other types of pre-surgical planning techniques and instrumentation.

Figure 1B:
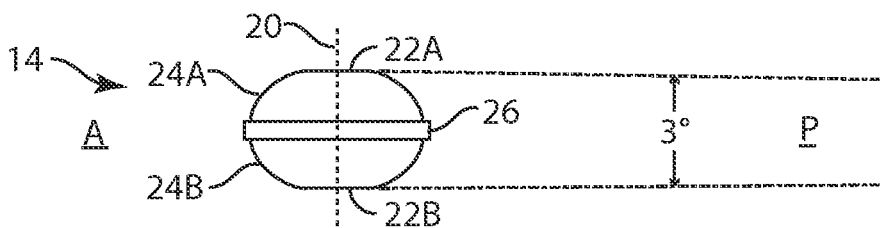
FIG. 1B illustrates the nucleus of FIG. 1A, with an offset maximum vertical axis that provides 3° of correction.
Figure 1C:
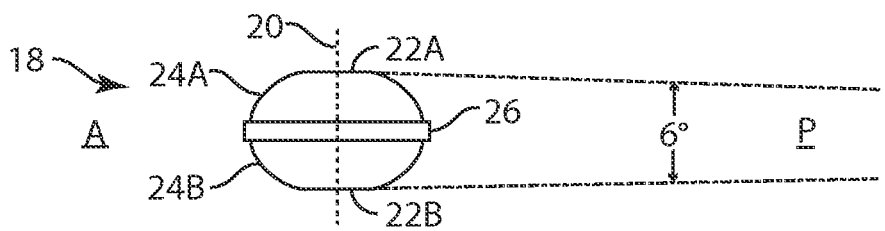
FIG. 1C illustrates the nucleus of FIG. 1A, with an offset maximum vertical axis that provides 6° of correction.

FIGS. 1A to 1C illustrate various examples of artificial disc nuclei where the nucleus is symmetrical, with a maximum central axis in the geometric center 20 of a nucleus 10. The reference letters A and P illustrate the anterior and posterior orientation, respectively, of the nuclei 10, 14 and 18. The nucleus 10 is generally spherical in shape and is truncated with a flattened portion 22A on the upper side of the nucleus 10 and another flattened surface 22B on the lower side. The nucleus also has upper and lower curved surfaces 24A and 24B, respectively, and a circumferential wall 26.

The flattened surfaces, as described above, can be advantageous because when the nucleus has a completely rounded surface, it cannot reliably maintain correction when exposed to the variable forces of the head and neck. A flattened surface incorporated into the central region of the nucleus can be used to solve this problem. The flattened surfaces have a contour different from the adjacent surface, and are formed in the nucleus body. The terms "flattened section" or "flattened surface" are used interchangeably and are meant to refer to any contour that is not the same as the adjacent surface(s) of the nucleus. Such a flattened surface can be planar or it be slightly convex or concave and have a radius of curvature different from the adjacent surface. Such a flattened surface could also be in the shape of a compound curve or other complex shape.

This flattened surface can be angled relative to the superior end plate of the inferior vertebral body (or vice versa, or both), with the height of the anterior end being greater than the height of the posterior end when lordotic correction is sought. The overall shape of the core can still be asymmetric, but the flattened surface can be incorporated to provide a reliable correction of the deformity. This flattened segment provides stabilization to resist the moments acting through the nucleus, i.e., if the flat is not of adequate size, there may be a tendency for the correction to disappear in the presence of an anterior load or for a hyper-lordotic over correction in the presence of a posterior load (during lordotic correction). Another advantage of the flattened segment is to provide surface contact over that area during small movements about the, neutral position of the device, which could help reduce wear on the device.

FIG. 1A illustrates a nucleus 10 that has not been adapted for lordotic correction because the upper and lower surfaces 22A and 22B are parallel to each other. In this nucleus, the axis 20 of greatest height falls in the center of the disc. In FIG. 1B, a nucleus 14 that provides 3° of correction is illustrated. This nucleus provides for lordotic correction. FIG. 1C illustrates another artificial disc nucleus 18 having a greater degree of deformity correction. When deformity correction is provided as shown in FIGS. 1B and 1C, the geometric center of the nucleus may shift to a location that is offset from the axis 20.

If the anterior/posterior directions are reversed, it provides a kyphotic correction. If the nucleus is rotated 90 degrees, a scoliotic correction is provided. In the illustration in FIG. 1C, the maximum vertical axis 20 is positioned to provide a correction of 6°. It is apparent that the nucleus can be adjusted to provide various degrees of correction and, in certain cases, if no degree of correction is needed. Alternatively, only one of the halves of the nucleus 10 may have a flattened portion, with the other half having an outer surface that is curved.

Figure 2A:
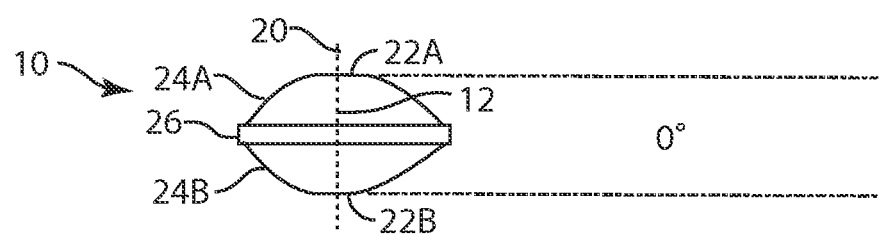
FIG. 2A illustrates an asymmetrical artificial disc nucleus with the maximum central axis in the geometric midline of the nucleus.
Figure 2B:
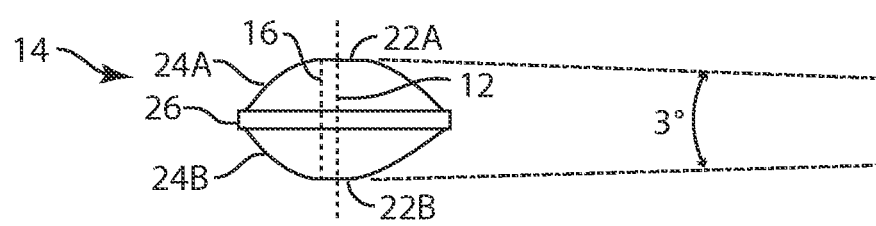
FIG. 2B illustrates the nucleus of FIG. 2A with an offset maximum vertical axis that provides 3° of correction.
Figure 2C:
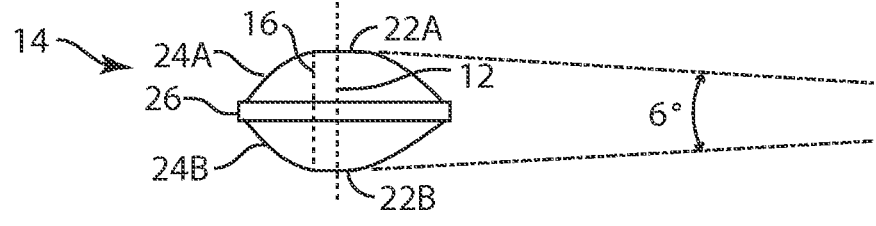
FIG. 2C illustrates the nucleus of FIG. 2A with an offset maximum vertical axis that provides 6° of correction.

In FIGS. 2A through 2C, asymmetrical ovoid embodiments of an artificial nucleus are shown. The nucleus comprises upper and lower surfaces 22A and 22B, which are "flattened" by virtue of the ovoid shape of the nucleus, upper and lower curved surfaces 24A and 24B, and a circumferential center portion 26. In the embodiments shown in FIGS. 2B and 2C, the maximum height axis 16 is asymmetrical with the geometric center 12 of the disc. In the nucleus shown in FIG. 2A, where there is no correction, the maximum vertical height is at the central vertical axis 12. In the nucleus shown in FIG. 2B, the maximum vertical axis 16 is positioned to provide an angle of correction of 3°. In the nucleus shown in FIG. 2C, the maximum vertical axis 16 is positioned to provide an angle of correction of 6°.

Figure 3:
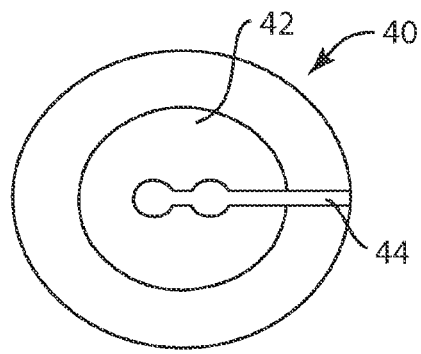
FIG. 3 is a top view of the embodiment of the artificial disc nucleus shown in FIG. 1A.

FIG. 3 is a top view of one example of a nucleus. This nucleus 40 comprises a central convex or flattened region 42, which includes a groove or slot 44. This groove or slot 44 enables the nucleus to slide onto the central keel or anchor of an end plate (not shown). While the nucleus 40 is shown as essentially circular, it is clearly apparent that it may take on other shapes such as an ovoid or ellipsoid shape. It is also clearly apparent that other types of anchor receiving means can be used. For example, the shape of the groove may vary or a snap-in or bayonet or dog-bone type of receptacle can be provided to anchor the nucleus in position. Those practiced in the art can provide additional locking methods including the addition of one or more parts to the core that provide an anchor.

Figure 4:
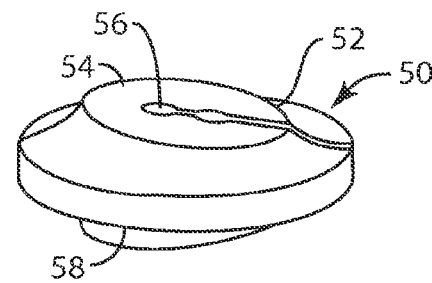
FIG. 4 is a perspective view of the embodiment of the artificial nucleus shown in FIG. 1A.

For deformity correction, the nucleus may take the form of a truncated curved body as shown in FIG. 4. For this embodiment, the nucleus 50 has an upper surface 52 that terminates in essentially flattened planar top 54. A slot 56 or a groove or opening of another appropriate shape, can be formed in upper surface 52 for receiving an anchor formed in the end plate. The lower surface 58 is typically an inverse of the upper surface. However, instead of being truncated with a flat surface as shown in FIG. 4, the bottom surface could be asymmetrically spherical or ovoid in shape.

Figure 5:
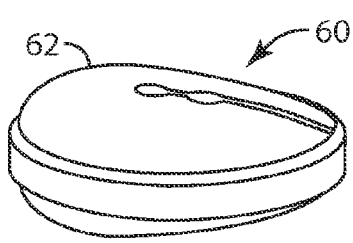
FIG. 5 is a perspective view of the embodiment of the artificial nucleus shown in FIG. 2A.

Alternatively, the nucleus may be circular, ovoid or egg-shaped having a non-central maximum vertical axis as shown in FIG. 5. In another embodiment, the nucleus could be essentially circular or asymmetrically spherical.

FIG. 5 illustrates an artificial nucleus 60 where the upper surface 62 is an asymmetric convex surface. Again, either the top or the bottom or both surfaces may be asymmetric.

For illustrative purposes, the nuclei in the figures have been shown adapted for lordotic correction. It is clearly apparent that the nucleus can have an asymmetric maximum height at the front (anterior), the rear (posterior) or the side (lateral). The asymmetrical nucleus of the present invention can be used to correct for various types of spinal misalignment including sagittal and coronal deformity.

The novel corrective nucleus of the present invention may be provided alone or it may be provided in combination with an upper end plate, a lower end plate or both an upper and a lower end plate.

Figure 6:
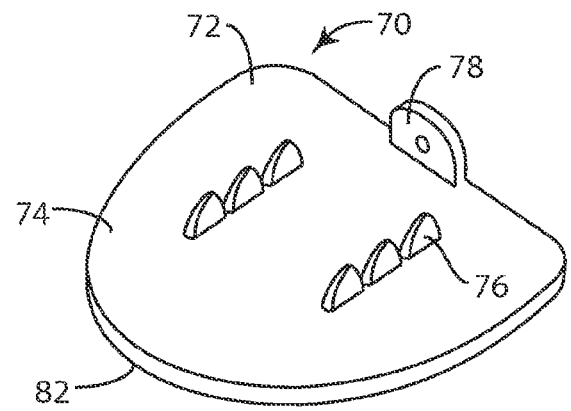
FIG. 6 is a perspective view of an outer surface of an end plate.
Figure 7:
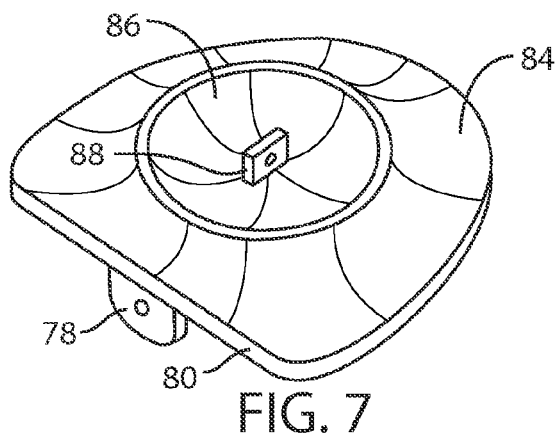
FIG. 7 is a perspective view of an inner surface of an end plate.
Figure 8:
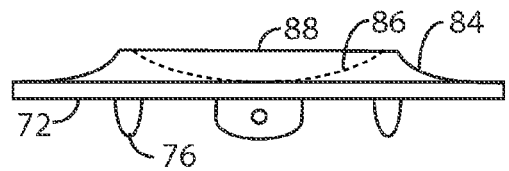
FIG. 8 is a front view of an end plate.

FIGS. 6 through 8 illustrate an exemplary artificial end plate 70 that can be used in conjunction with the nucleus to provide a novel artificial disc unit. An artificial end plate according to the present invention comprises an inner surface with a concave bearing surface for receiving the convex surface of an artificial disc. The outer, or bone contacting, surface is essentially flat.

To accommodate some previously known end plates, it was necessary to spend a significant amount of surgical time to prepare the vertebrae to the appropriate shape to accommodate the artificial end plate. FIG. 6 shows an end plate 70 with a flat outer surface 72 that enables the end plate to slide on the surface of the vertebra. One or more unidirectional keels 76 are formed on the outer surface 72 to provide for immediate fixation. The keels may be placed centrally or parasagittally. Fixation can be enhanced by incorporating onto the outer surface 72 a suitable coating 74, such as porous titanium, a calcium phosphate or the like, to promote bony ingrowth for long term stability.

A stop member 78 can be provided at the anterior edge 80 of the end plate. The stop member prevents the prosthesis from migrating posteriorly and possibly impinging on the spinal cord. An essentially semi-circular wall 82 joins the outer surface of the end plate to the inner surface. The thickness of 82 may vary with increased thickness anteriorly, posteriorly or parasagittally, as discussed further below. The inner surface 84 is shown in greater detail in FIG. 7.

The inner surface 84 of the end plate articulates with the nucleus. In the embodiment shown in FIG. 7, this inner surface has a concave region 86, which receives the nucleus. An anchor 88 is provided in the center of the concave region 86 for positioning the nucleus and preventing it from migrating. The anchor 88 can be generally rectangular in shape with rounded edges, as shown, avoiding premature wear and cutting into the nucleus. FIG. 8 illustrates a front view of the end plate showing the outer surface 72 having two parasagittal keels 76 and the inner surface 84 having a concave region 86 and a central anchor 88.

Figure 9:
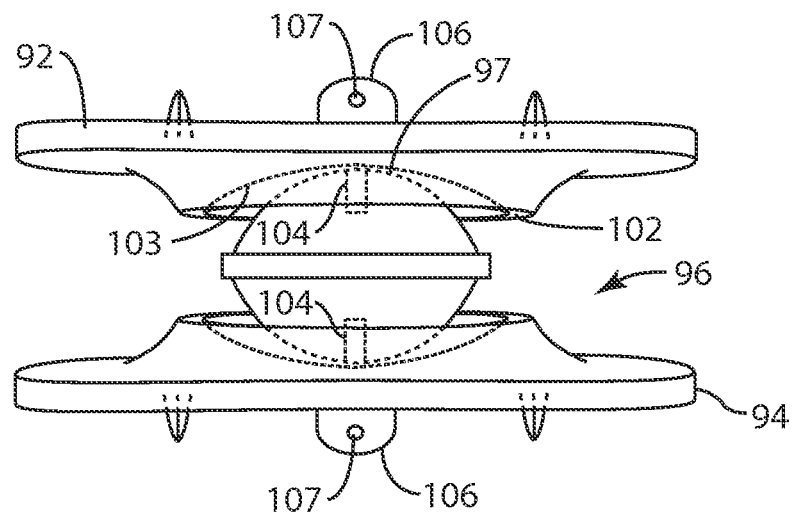
FIG. 9 is a front view of a spinal disc device with the nucleus shown in FIG. 1A.
Figure 10:
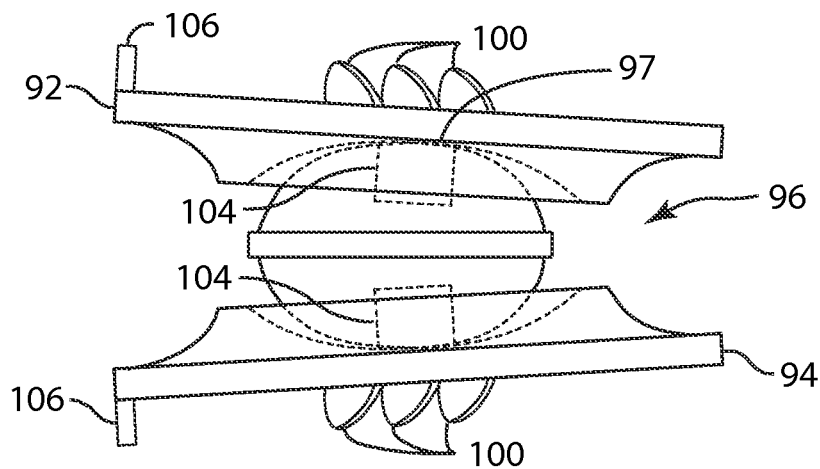
FIG. 10 is a side view of the spinal disc device of FIG. 8.

FIGS. 9-12 illustrate a nucleus and end plates described above assembled into a TDR implant. FIGS. 9 and 10 show the use of a nucleus 96 with a truncated cylinder shape and a flattened portion 97 on the superior side of the nucleus as described above, in conjunction with FIGS. 1A-1C, and FIGS. 11-12 show the same design with a nucleus 96 having an ovoid shape as shown in FIGS. 2A-2C. In these figures, a complete spinal disc prosthesis 90 comprising a superior end plate 92, an inferior end plate 94 and an artificial disc nucleus 96 is provided. The end plates and nucleus can be provided in different sizes to accommodate differences in anatomy. The end plates and various nuclei can be provided in a kit to the surgeon so that the appropriate sized components can be selected and used when the final size is determined. The end plates may be fabricated of titanium or titanium alloy, chrome-cobalt-molybdenum (CoCrMo), cobalt 28 chromium molybdenum, cobalt chrome, ceramics or other material suitable for spinal prosthetic implants.

The end plates have two distinct surfaces. The outer surface 98 is the surface that contacts the vertebral end plate. The outer surface is essentially flat enabling it to easily contact the surface of the natural vertebral end plate. The flat surface can be porous and incorporate a suitable treatment, such as porous titanium, a calcium phosphate or other types of known treatments such as coatings, plasma sprays, and structural changes to the surface, that promote bony ingrowth or ongrowth for long-term stability. At least one parasagittal keel 100 is formed on the outer surface of each end plate to provide immediate fixation.

Figure 9A:
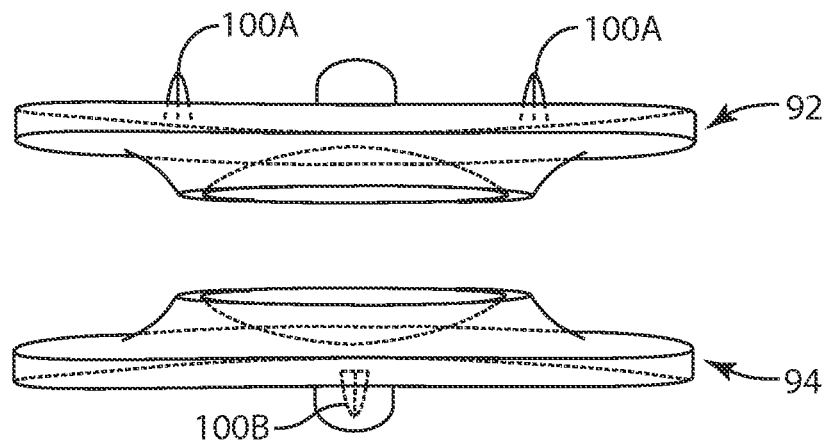

As shown in FIGS. 9-12, three parasagittal keels 100 are aligned with each other and located along both sides of the outer surface of the end plates. Alternatively, as shown FIG. 9A a similar end plate design with an upper end plate 92 and a lower end plate 94 have an offset keel configuration with a pair of aligned parasagittal keels 100A formed on the outer surface of the upper end plate and a centrally-located row of aligned keels 100B formed on the outer surface of the lower end plate 94. This latter arrangement is believed to be advantageous because, with the upper and lower keels being offset from each other, the end plates should have greater stability and result in less stress on a vertebra where multiple implants are used.

Figure 11:
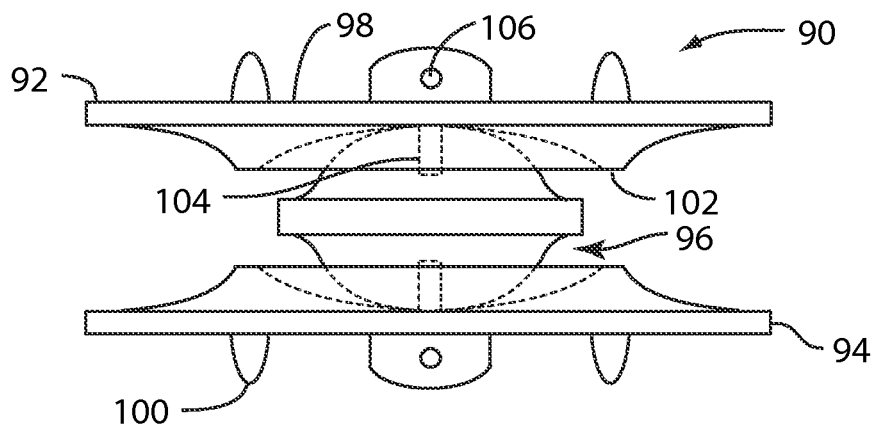
FIG. 11 is a front view of a spinal disc device with the nucleus shown in FIG. 2A.
Figure 12:
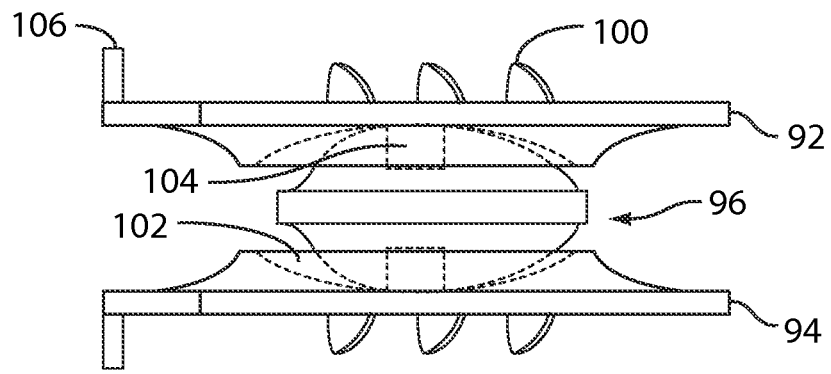
FIG. 12 is a side view of the spinal disc device of FIG. 8.

Referring back to FIGS. 9-12, the inner surface 102 of each of the end plates has a concave region 103 or bearing surface that articulates with the nucleus. An anchoring protrusion 104 projects outwardly from the concave region, which provides an anchor for the nucleus and restricts posterior translation. Both the superior and the inferior end plates have flanges 106 for preventing the end plates from migrating into the spinal canal. The end plates can have holes 107 for allowing the end plates to be connected to the adjacent vertebrae through either metallic or bioabsorbable screws (not shown) that can be inserted through holes 107. FIGS. 9 and 11 illustrate front views of the prosthesis and FIGS. 10 and 12 illustrate side views.

Figure 13A:
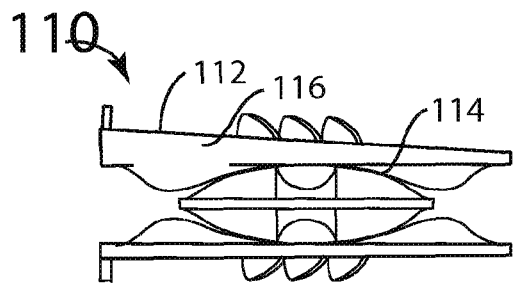
FIGS. 13A and 13B illustrate an embodiment of an artificial spinal disc prosthesis where the end plates may be adapted for lordotic correction.
Figure 13B:
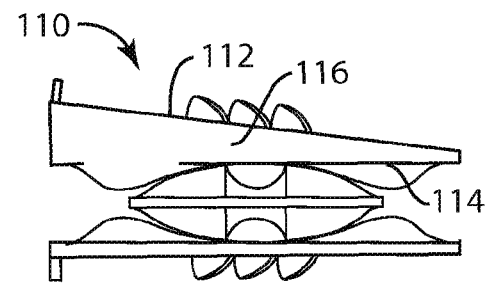
Figure 14A:
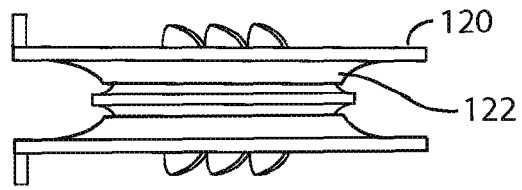
FIGS. 14A, 14B, and 14C illustrate other embodiments where the end plates can be adapted for lordotic correction.
Figure 14B:
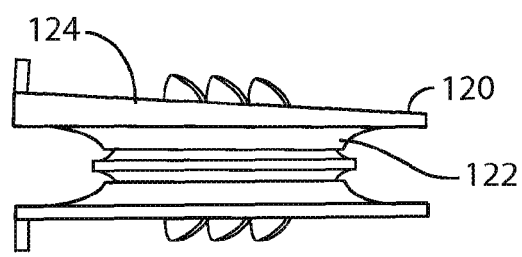
Figure 14C:
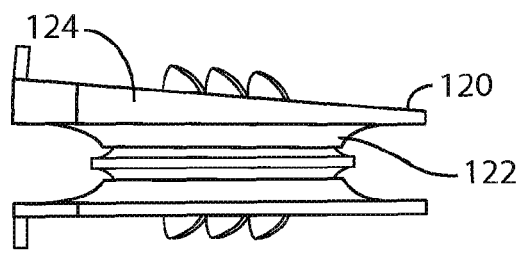

In another aspect of the invention, shown in FIGS. 13A-13B and 14A-14C, spinal deformity can be addressed by providing an artificial spinal disc prosthesis where correction is provided in the end plates. Corrective end plates may be provided alone, in combination with a symmetrical artificial nucleus that has flattened surfaces as described above on both the top and bottom of the nucleus, as shown in FIGS. 13A-13B, or in combination with an asymmetrical nucleus that has flattened surfaces as described above on both the top and bottom of the nucleus, as shown in FIGS. 14A-14C.

Correctional end plates are shown in FIGS. 13A-13B and 14A-14C. The degree of correction can be achieved by altering the inner (nucleus-contacting) side of the end plate or the outer (vertebral-contacting) side of the end plate. As shown in FIGS. 13A-13B, the end plate 110 comprises an outer (bone-contacting) surface 112, an inner surface 114, and a perimeter wall 116 connecting the outer and inner surfaces. The height of the perimeter wall 116 may vary according to the degree and type of correction required. For example, FIG. 13B illustrates an end plate adapted for a greater degree of correction than the end plate of FIG. 13A. The positioning of the variable height can be adjusted to treat different conditions such as lordosis, kyphosis or scoliosis. The inner surface may be shaped to receive the nucleus, and the height of the end plate can be adjusted according to the degree of correction required.

Alternatively, as shown in FIGS. 14A-14C, the outer surface 120 and the inner surface 122 may be essentially planar and the height is adjusted as the outer and inner surfaces become increasingly non-parallel as a result of variation in the height of the perimeter wall 124. FIGS. 14A through 14C illustrate increasing degrees of correction, respectively. An advantage of having an essentially planar outer, or vertebral-contacting, surface is that the device is easier to insert and requires less operating time to prepare the vertebral surface as compared to traditional artificial disc devices.

Figure 15:
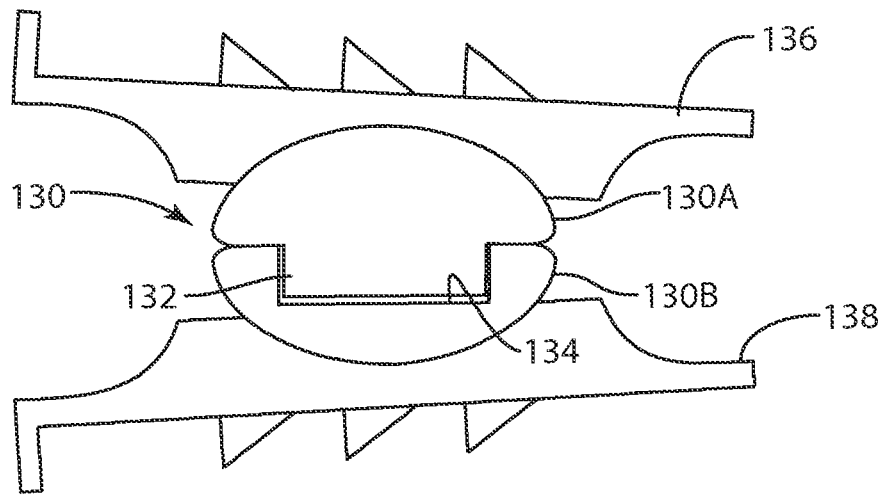
FIG. 15 is a side view of another embodiment which provides for all directions of movement.
Figure 16A:
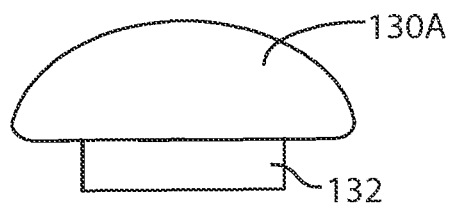
FIGS. 16A and 16B illustrate the two sections of the nucleus of the embodiment of FIG. 15.
Figure 16B:
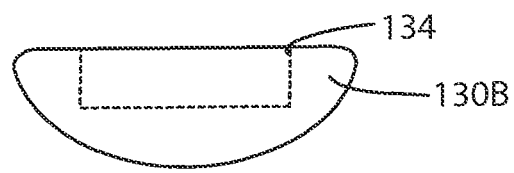

FIGS. 15, 16A and 16B illustrate another embodiment of the invention, which provides for all directions of movement, flexion/extension, lateral bending, and rotation about the symmetrical axis. In this design, the nucleus 130 is formed in two sections 130A and 130B. A post 132 is formed on the inner surface of one section 130A, and fits in an opening 134 that is formed on the inner surface of the other section 130B to provide for relative rotational movement between the two sections 130A and 130B. The post 132 and opening 134 can be formed on either section of the nucleus 130. The post and opening can be of any suitable size, and can be perpendicular to the opposing surfaces of the nucleus sections 130A and 130B, or be tilted at an angle off horizontal to orient the axis of axial rotation with the anatomically correct axis and provide a deformity correction.

In this configuration, the contact surfaces between the nucleus 130 and end plates 136 and 138, are designed to have the same corresponding asymmetrical contours at the preferred angle between them, as shown in FIG. 15. Because there is only relative movement between the nucleus and the end plates in the anterior/posterior and medial/lateral directions, greater surface contact between the nucleus and the respective end plates is possible in order to transmit rotations of the end plates to the nucleus so that the two halves 130A and 130B, of the nucleus 130 will rotate with respect to each other, rather than having the end plates 136 and 138, rotate on the outer surface of the nucleus 130.

Figure 17:
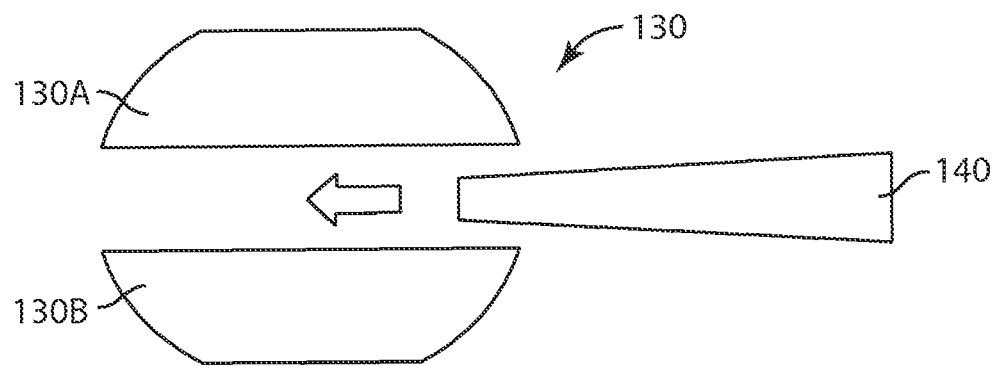
FIGS. 17 and 18 illustrate another embodiment of the invention in which the nucleus is formed of upper and lower sections with an intermediate section.
Figure 18:
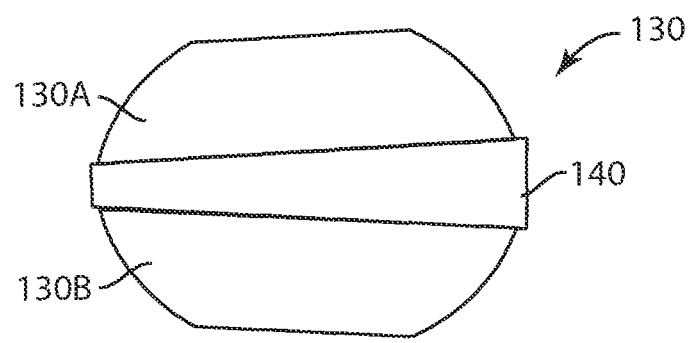

FIGS. 17 and 18 show another embodiment of the invention where instead of forming the nucleus 130 of a single piece of material, it can be formed of upper and lower sections 130A and 130B, with an intermediate section 140, that is either flat or wedge-shaped as shown in FIG. 17, fixed to the upper and upper and lower sections. The intermediate section 140 can provide the nucleus with the appropriate degree of correction as shown in FIG. 18, instead of providing wedge-shaped end plates as discussed above. In a related embodiment of the invention, the nucleus 130 is essentially cut in half and has a flat inferior surface. This can be applied to the embodiment seen in FIGS. 17 and 18, where the section 130B is removed, leaving the inferior surface of intermediate section 140 articulating with the inferior end plate. By varying the configuration of the intermediate section 140, deformity correction can be achieved.

Figure 19:
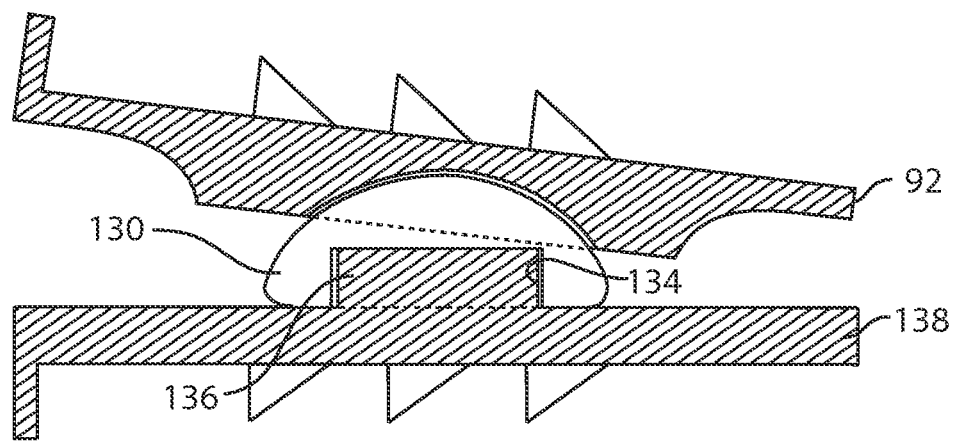
FIG. 19 illustrates another embodiment of the invention in which the nucleus is cut in half and has a flat lower inferior surface.
Figure 20:
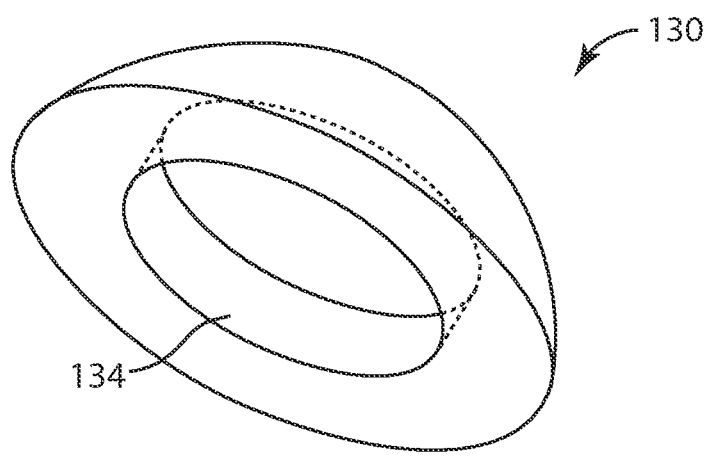
FIG. 20 is a schematic view of the nucleus of FIG. 19.

FIGS. 19 and 20 show another embodiment of the invention where the nucleus 130 is essentially cut in half and has a flat lower inferior surface. This shape can be used to resist expulsion of a nucleus with an ovoid/asymmetric shape, which could occur when the ovoid shape of the nucleus causes the end plates to tilt relative to each other to provide correction. As shown, the bottom surface of the nucleus 130 is flat and is formed with a circular opening 134 that is shaped and positioned to receive a post 136 formed on the opposing surface of the lower end plate 138 for allowing relative rotational movement between the nucleus 130 and the end plate 138. Alternatively, the nucleus could have the flat surface and opening 134 on its upper or superior surface, instead of being on the lower surface as shown. In this embodiment, the nucleus is preferably asymmetrical as shown in FIG. 19.

Figure 21:
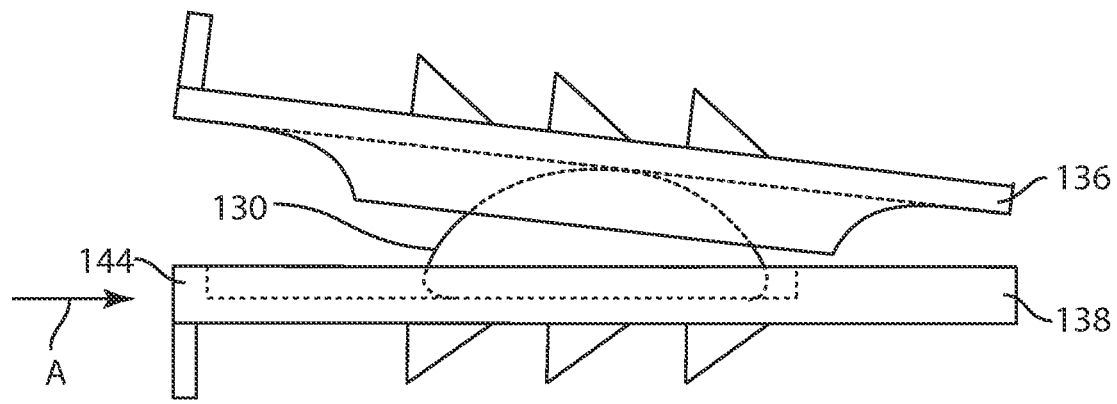
FIG. 21 illustrates a modification of the embodiment of FIG. 19.
Figure 22:
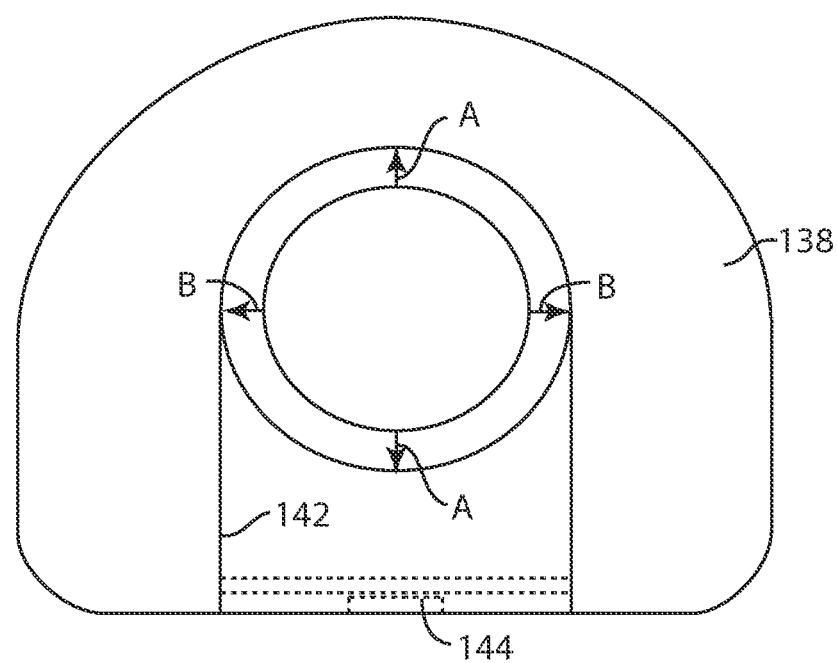
FIG. 22 is a an underside view of the nucleus of FIG. 21.
Figure 23:
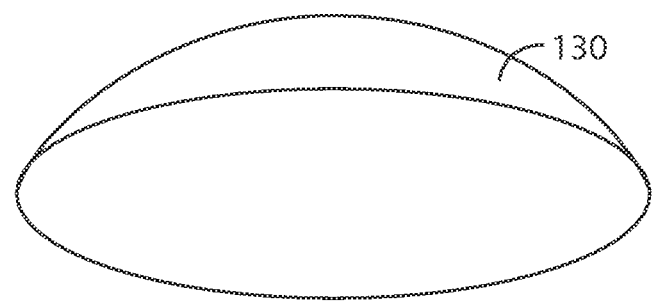
FIG. 23 is a schematic view of the nucleus of FIG. 21.
Figure 24:
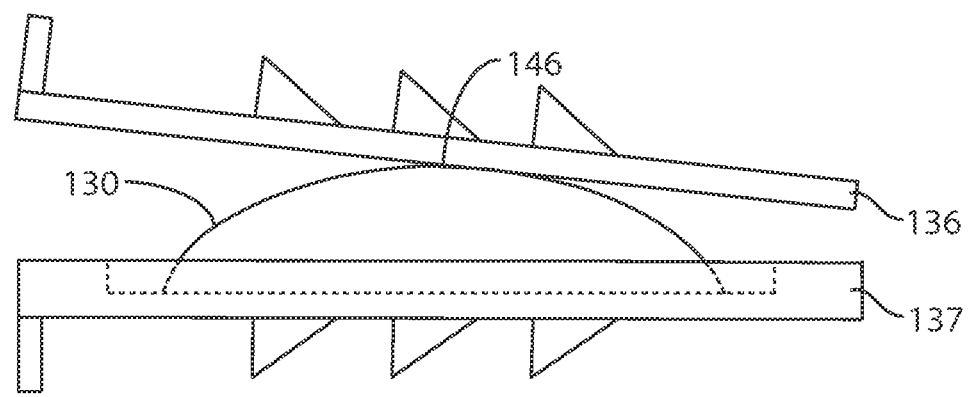
FIG. 24 illustrates a modification of embodiment of FIG. 19.

A modification of the configuration in FIGS. 19 and 20, is shown in FIGS. 21 through 24, where the nucleus 130 is positioned in a slot or trough 142 formed in the upper surface of the lower end plate 138. As shown in FIG. 21, the undersurface of the upper end plate 136 is contoured to match the nucleus. Alternatively, as shown in FIG. 24, the undersurface of the end plate 136 can be flat and engage a flattened upper surface 146 of the nucleus 130.

The trough can be larger than the nucleus in both the anterior/posterior and medial/lateral directions to allow for a desired amount of translation in those directions as shown by the arrows A and B in FIG. 22. The trough can be open on the posterior or anterior end to allow the nucleus to be inserted simply by sliding it into the trough, as shown by the arrow A in FIG. 21. In this way, the nucleus can be inserted without undue distraction of adjacent vertebrae. The nucleus can be prevented from moving out of the trough by providing a stop 144 of any suitable size and shape. FIG. 23 is a schematic view of the nucleus 130 that is inserted in the trough in FIG. 21.

Another embodiment of the invention is shown in FIGS. 25-31, where the nucleus 130 is elongated, with a flattened section 150 that is a partial cylinder with curved sections 152 and 154 on both sides of the flattened section. It is believed that this design, when mated with a cylindrical surface 156 on the interior of the upper end plate 136, shown in FIG. 29, will provide better wear characteristics because it will have surface contact during medial/lateral bending and line contact during flexion/extension.

Figure 25:
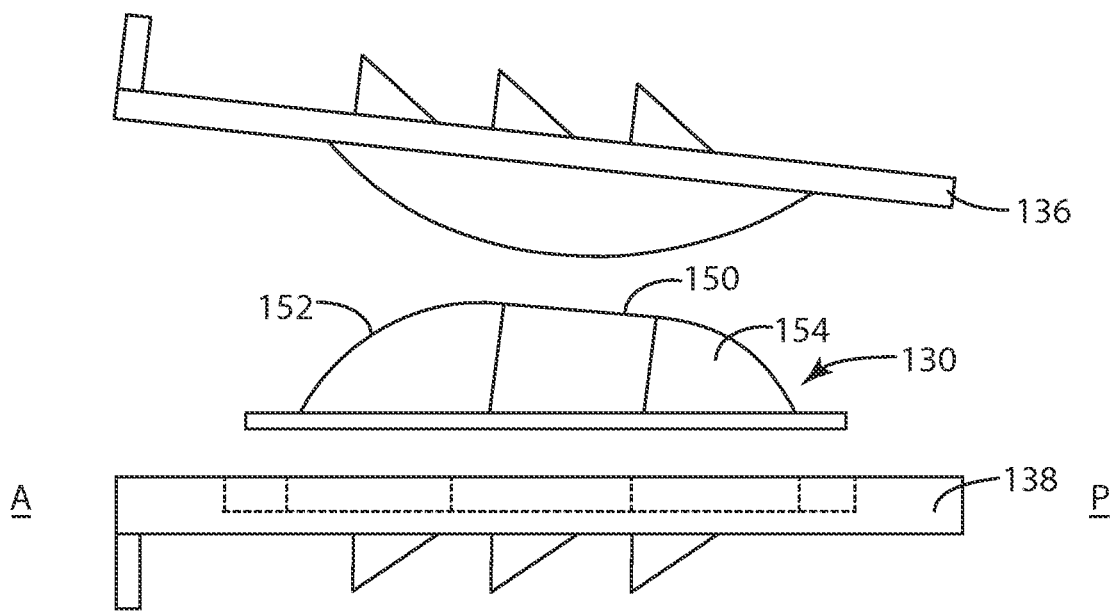
FIGS. 25-31 illustrate another embodiment of the invention in which the nucleus is elongated with a flattened section in the center.
Figure 26:
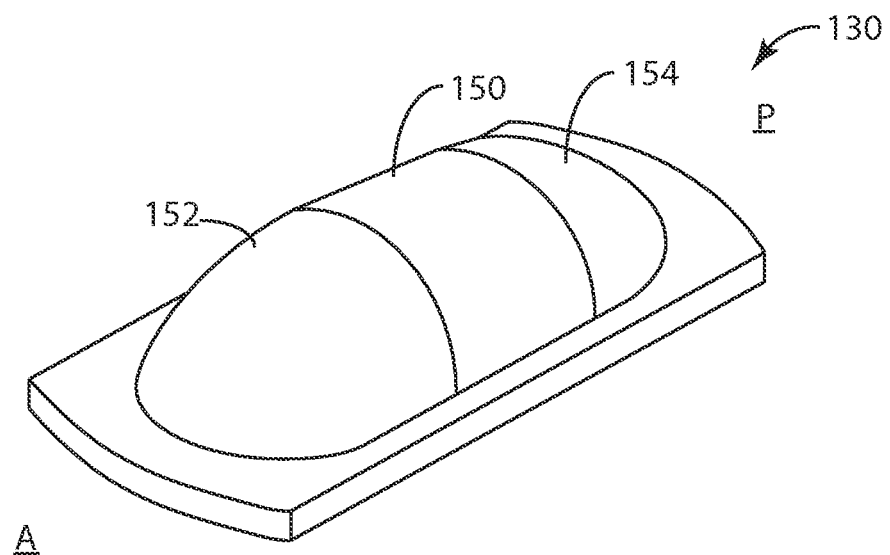

The elongated shape of the nucleus 130 is illustrated in FIGS. 25 and 26, which show that the nucleus has a round cross section with constant medial-lateral radius from anterior to posterior (A-P), with the flat section 150 in the middle being oriented to provide a correction angle as described above, for the flatted portions on the other embodiments of the nucleus. The interior surface 156 of the upper end plate 136 has a cylindrical shape with the same constant radius in the anterior/posterior direction as the nucleus.

Figure 31:
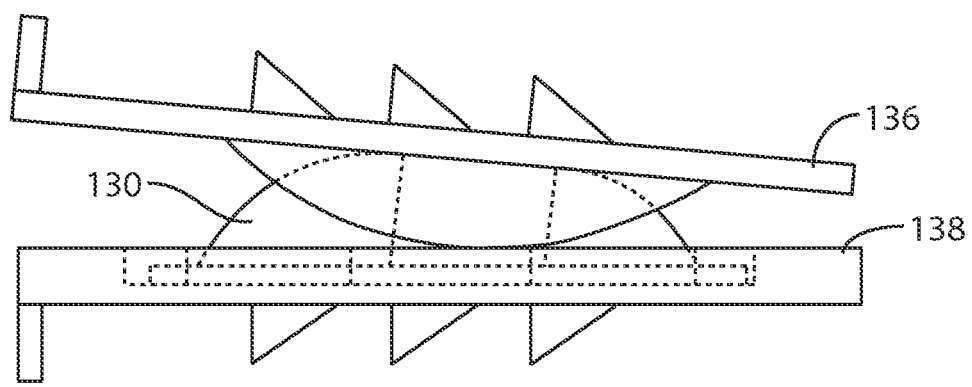

In the neutral position, the cylindrical surface 156 mates with the flattened section 150 of the nucleus 130, and sits at an angle that provides a deformity correction as shown in FIG. 31. In this position, there is surface contact between the end plate 136 and the nucleus 130. During medial/lateral bending, there is also surface contact between the end plate and nucleus. During flexion/extension, with or without lateral bending, there is line contact between the end plate and nucleus. This configuration of core and end plate will always have line or surface contact, thus reducing the wear potential from point contact in some of the previous designs.

Figure 27:
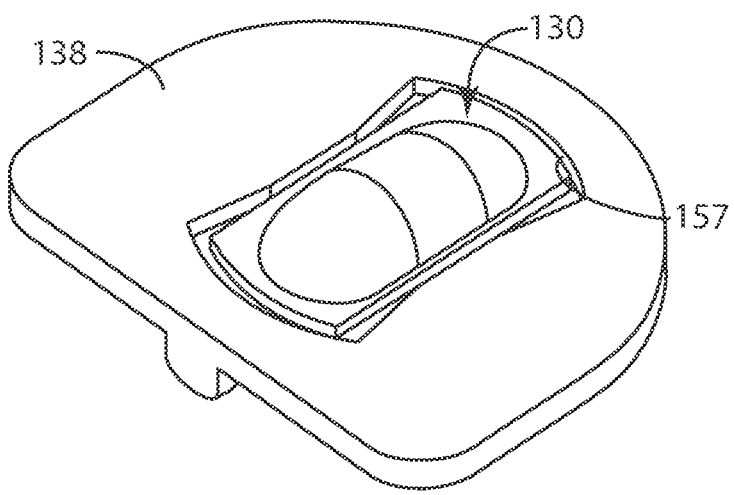
Figure 28:
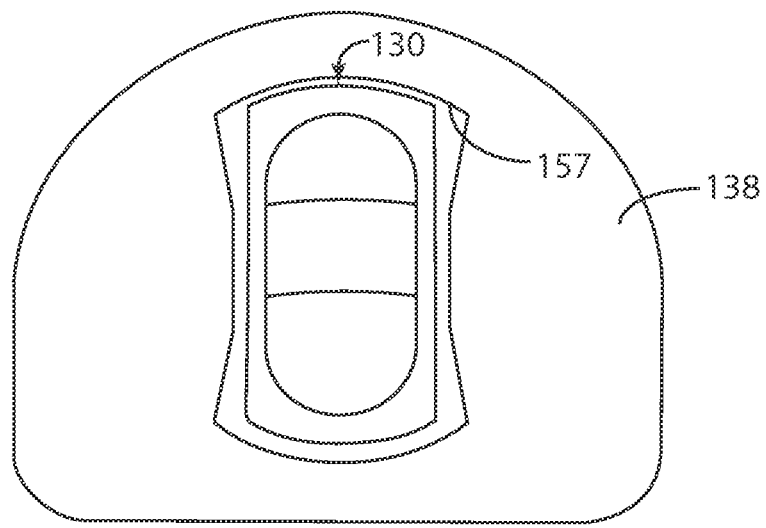
Figure 29:
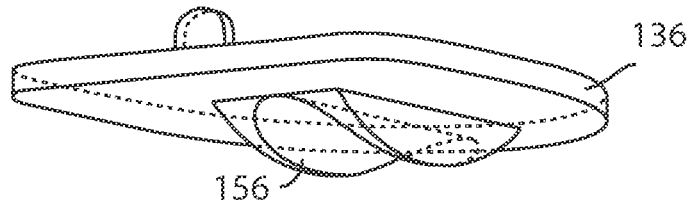
Figure 30:
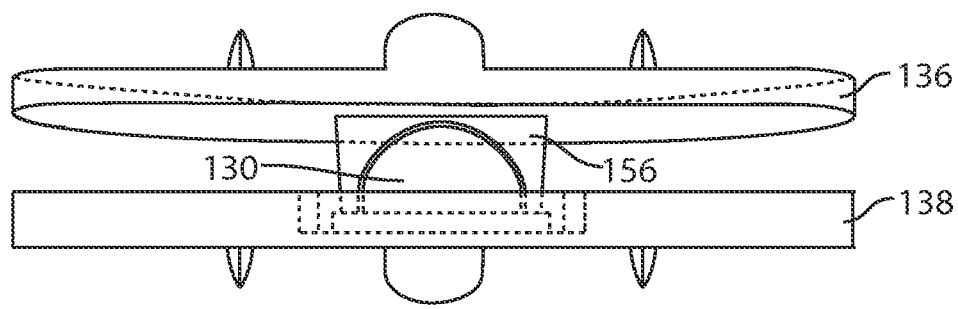

The elongated shape of the nucleus 130 allows for the end plate 138 to have a trough 157 in the shape of a "bow tie" as shown in FIGS. 27 and 28. This shape allows for axial rotation with stops beyond the limits of normal motion. The shape is oversized relative to the nucleus 130 by an appropriate amount to allow limited anterior/posterior and medial/lateral translation. Additionally, the bottom surface of the trough 157 can be rounded upwardly at the medial/lateral sides in FIG. 30 (not shown), so that as the nucleus 130 rotates it is "cammed" up causing a distraction of the device that forces the vertebral bodies apart and loads the tissues between them resulting in a gradual stop to the motion. Translation of the nucleus 130 within the trough 157 will tend to preserve the mobile instantaneous axis of rotation of the natural disc.

Figure 32:
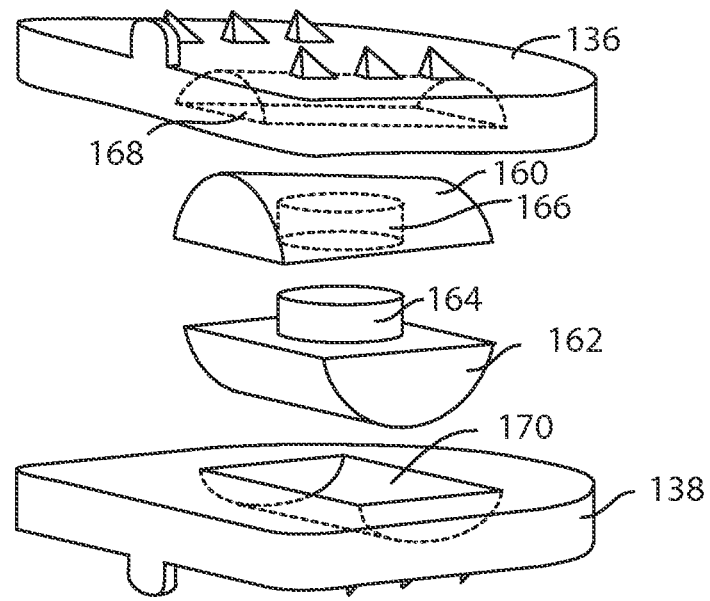
FIGS. 32 and 33 illustrate another embodiment of the invention which utilizes a universal joint.
Figure 33:
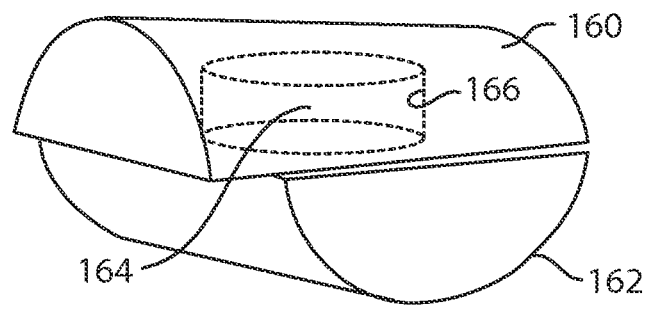

FIGS. 32 and 33 show another embodiment of the invention, which utilizes a universal joint formed of a pair of cylinders 160 and 162 that rotate relative to each other about a central post 164 that projects from one of the cylinders 162 and engages an opening 166 in the other cylinder 160. The cylinders 160 and 162 are oriented perpendicular to each other and engage cylindrical surfaces 168 and 170, respectively, in the adjacent end plates 136 and 138. This design provides for three anatomical axes of rotation. Because of the independence of each axis of rotation, any correction provided by the shape of the nucleus that is formed of the two cylinders will result in rotation to compensate for the correction and a return to the uncorrected neutral position. Alternatively, the cylinders 160 and 162 may be shaped similarly to the elongated nucleus 130 shown in FIGS. 25-27, or another suitable shape with a flat inferior surface.

Figure 34:
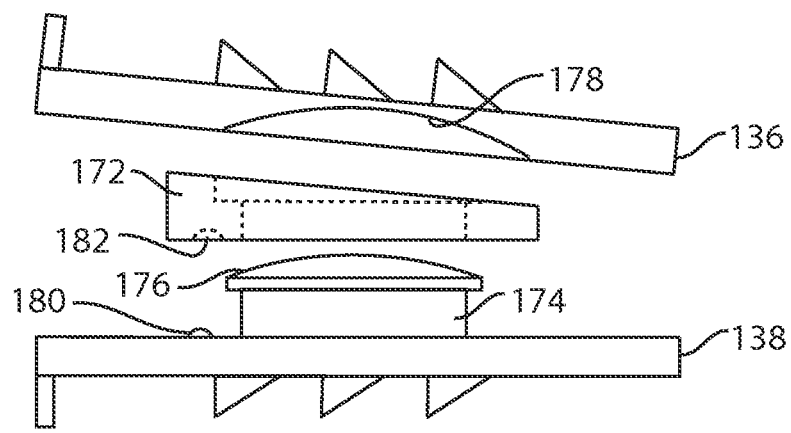
FIGS. 34-36 illustrate another embodiment of the invention in which a resilient ring and a post provide for relative motion between the end plates.
Figure 35:
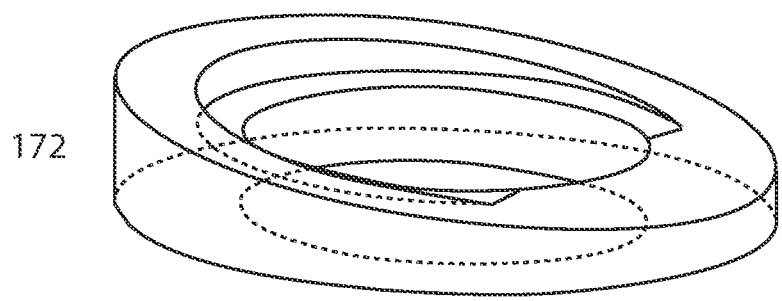
Figure 36:
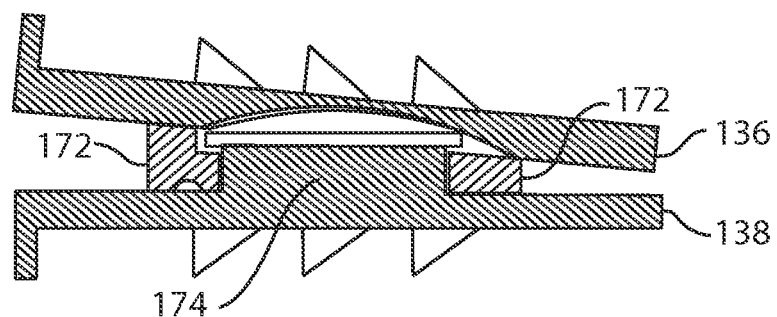

Another embodiment of the invention is shown in FIGS. 34-36, where a resilient ring 172 and a post 174 that has a rounded top portion 176 provide for relative motion between the end plates and for the desired angle of correction. The ring 172 is shown in detail in FIG. 35. The ring 172 can be wedge shaped as shown in order to provide the desired amount of correction, or it can be flat (not shown) if no correction is desired. A projection 180 can be formed on the upper surface of the lower end plate 138 to mate with an opening 182 in the ring 172 in order to prevent the ring 172 from moving relative to the lower end plate once the ring is in its desired position.

The upper end plate 136 has a cavity 178 that can be contoured to match the shape of the rounded top portion 176. The ring 172 is shaped so that the end plate 136 will ride on the ring 172 during "normal" ranges of motion, or through regular activities. However, when the normal ranges of motion are exceeded, then the ring 172 will compress and the upper end plate 136 will engage the post 174 causing the adjacent vertebrae to distract and thereby provide a gradual stopping motion or "anatomically-derived gradual stopping." Alternatively, the post 174 could be designed to serve as the primary load carrying part of the articulation by riding in the cavity 178. In this design, the deformity correction force is only provided by compressing the ring 172. This design would have the advantage of reducing material stresses in the elastomer ring and creep.

Figure 37:
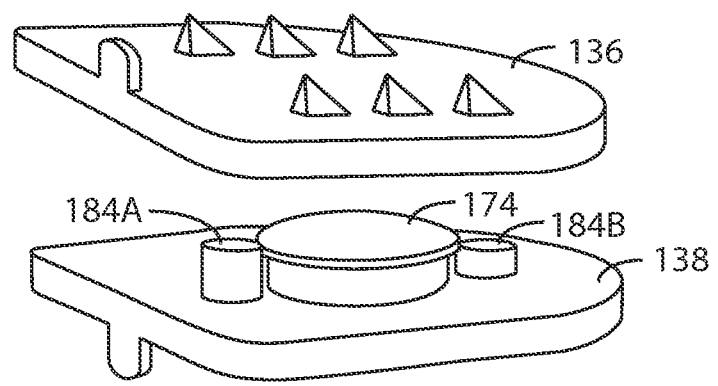
FIG. 37 illustrates a modification of the embodiment of FIG. 34.

As shown in FIG. 37, instead providing the ring 176, the same result could be achieved by providing two or more stops 184A and 184B, formed of a resilient material, between the two end plates. The stops 184A and 184B can be mounted on the upper surface of the lower end plate 138. One of the stops 184A can project upwardly a greater distance than the other stop 184B in order to provide the desired correction.

Figure 38:
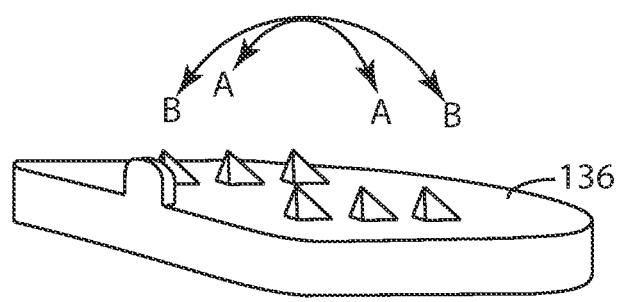
FIGS. 38 and 39 illustrate another embodiment of the invention in which the nucleus is shaped to provide medial/lateral correction.
Figure 38:
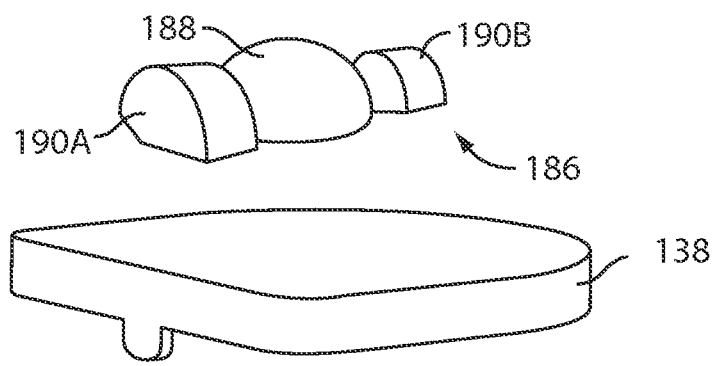
Figure 39:
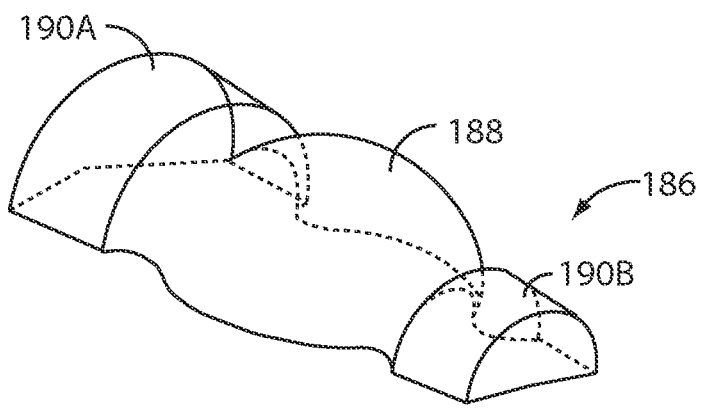

Another embodiment of the invention is shown in FIGS. 38 and 39, where a nucleus 186 is provided that is formed of a resilient material that is shaped so that the nucleus provides medial/lateral rotation, but requires deformation of the material during flexion and extension. This is accomplished by proving a central portion 188 that is spherical or ovoid in shape and "flattened" adjacent end portions 190A and 190B that are cylindrical, which extend the flattened end portions around the circumference of the nucleus at both ends. The upper end plate has a cavity (not shown) that has a contour that is similar in shape to the nucleus 186. A trough (not shown) similar to the one in FIGS. 27 and 28 can be formed in the lower end plate 138.

For medial/lateral movement in the direction of the arrows A-A, the upper and lower end plates will rotate relative to each other through rotational movement of the upper end plate on the nucleus 186. However, flexion/extension in the direction of arrows B-B will occur only through deformation of the nucleus 186. Alternatively, the nucleus 186 can be rotated 90° on the lower end plate 138 so that so that the end plate 136 will rotate on the nucleus during flexion/extension and the nucleus will deform during medial/lateral movement. The end portion 190A has a larger diameter than the end portion 190B to provide for the desired amount of correction. As shown, the nucleus has been shaped so the resilience of the nucleus varies over its length. However, the nucleus could be formed of materials having varying degrees of resiliency along its length to achieve the same results.

Figure 40:
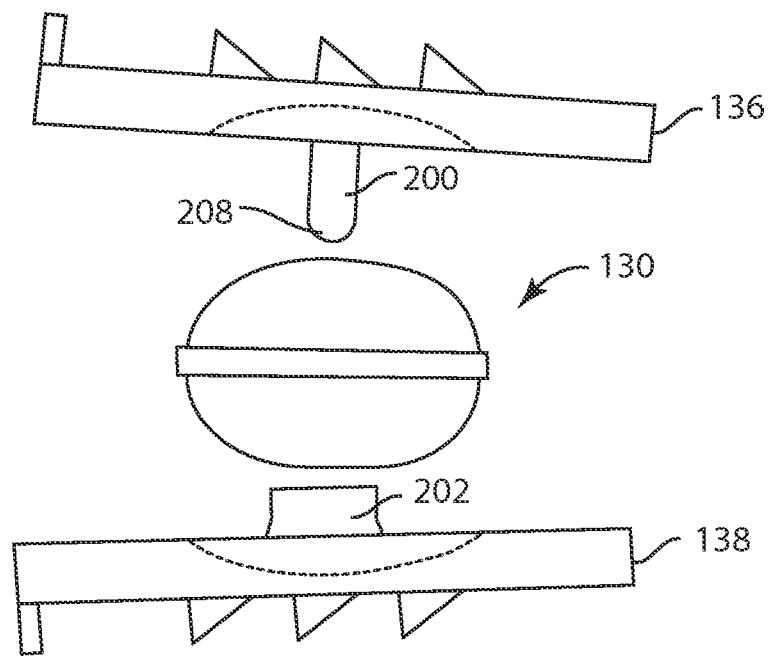
FIGS. 40-43 illustrate another embodiment of the invention in which the end plates are provided with stops outside the normal range of motion.
Figure 41:
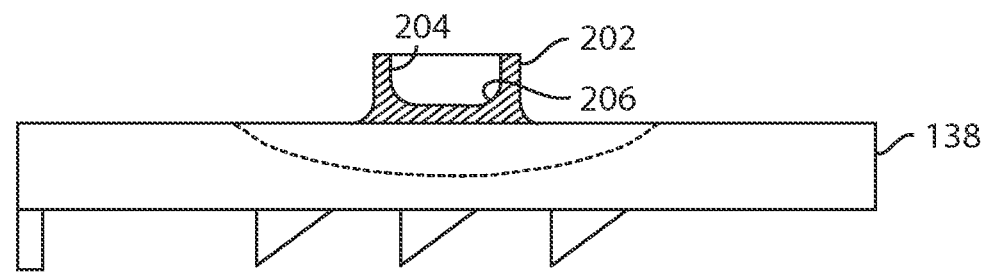
Figure 42:
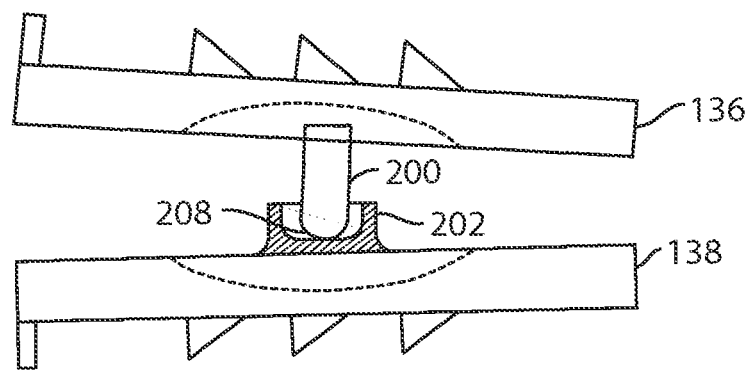
Figure 43:
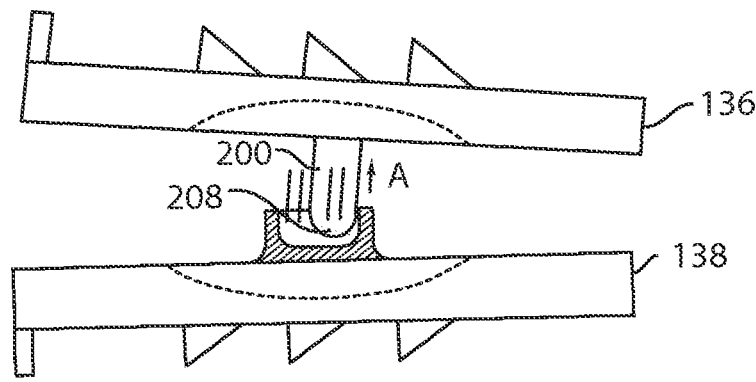

FIGS. 40-43 illustrate another embodiment of the invention where the end plates 136 and 138 are provided with stops outside of the normal range of motion, which also utilize the concept of "anatomically-derived gradual stopping" discussed above in conjunction with FIGS. 34 and 35. This type of stop can be added to any design that employs the use of end plates. This aspect of the invention is based on duplicating how the human body moves and then designing the cooperating surfaces to mimic those motions as closely as possible. As shown in FIG. 40, the end plate 136 has a post 200 on its lower surface that engages pocket 202 formed in the upper surface of the lower end plate and 138. Preferably, a pair of posts and pockets are provided on opposite sides of the nucleus 130.

As shown in FIGS. 40-43, the pocket 202 has a slot 204 in it with a curved surface 206 that is engaged by the lower end 208 of the post 200. As the end plates 136 and 138 move in the anterior/posterior direction relative to each other during extension/flexion, the lower end 208 of the post rides along the curved surface 206. As the post reaches the outer limits of travel the lower end 208 will begin riding up the gradually curved section of the surface 208, which causes distraction between adjacent vertebrae as illustrated by the arrow A in FIG. 43 and loads the tissues between them, resulting in a gradual stop to the motion.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A nucleus for an artificial disc for replacing the natural disc of a human spine and being adapted to fit between and move relative to first and second end plates that are attached to adjacent vertebrae, the nucleus comprising:
   a nucleus body having superior and inferior bearing surfaces for engaging cooperating bearing surfaces formed on the first and second end plates, respectively, the superior bearing surface facing opposite the inferior bearing surface;
   said superior bearing surface having a first curved portion convexly curved in the sagittal plane, wherein a first planar portion is formed on the first convex curved portion for engaging and rotationally articulating relative to a cooperating bearing surface on the first end plate to maintain a correction orientation of at least one of the end plates relative to the nucleus, the first planar portion configured to extend across the intersection of the coronal and the sagittal planes, the coronal and the sagittal planes defined relative to the nucleus body such that the intersection defines a vertically extending geometric center axis of the nucleus body, the nucleus further comprising a circumferential flange positioned between the inferior and superior bearing surfaces, the flange projecting radially away from the nucleus body.

2. The nucleus of claim 1, wherein the second bearing surface is planar.

3. The nucleus of claim 1, wherein the nucleus body is asymmetrical in the sagittal plane along the midline of the nucleus body, relative to the vertically extending geometric center axis of the nucleus body.

4. The nucleus of claim 1, wherein the nucleus has a horizontal axis and the first planar portion is formed at an angle other than parallel relative to the horizontal axis for maintaining the correction orientation of the artificial disc when the nucleus engages the end plates.

5. The nucleus of claim 4, wherein the angle is between 3 and 6 degrees.

6. The nucleus of claim 1, wherein the nucleus body has a second curved portion formed on the second bearing surface.

7. The nucleus of claim 6, wherein a second planar portion is formed on the second curved portion.

8. The nucleus of claim 1, wherein the nucleus body is formed of a polymeric material.

9. The nucleus of claim 1, wherein the nucleus body is formed of a resilient material.

10. The nucleus of claim 1, wherein the nucleus body further comprises a circumferential wall positioned between and separating the superior bearing surface and the inferior bearing surface.

11. The nucleus of claim 1 and further including first and second end plates adapted to be attached to adjacent vertebrae, the nucleus body being positioned between the end plates to form a total disc replacement.

12. A nucleus for an artificial disc for replacing the natural disc of a human spine and being adapted to fit between and move relative to first and second end plates that are attached to adjacent vertebrae, the nucleus comprising:
a non-resilient nucleus body having a first bearing surface and a second bearing surface, the first and second bearing surfaces configured to engage and articulate relative to the respective first and second end plates, the first bearing surface comprising a first curved portion convexly curved in the sagittal plane, a planar first portion formed on the first convex curved portion, the planar first portion configured to extend across the intersection of the coronal and the sagittal planes, the coronal and the sagittal planes defined relative to the nucleus body such that the intersection defines a vertically extending geometric center axis of the nucleus body; a planar second portion formed on the second bearing surface, the planar first portion opposite the planar second portion, a maximum height axis extending between the first and second planar portions at the maximum height of the nucleus body;
wherein the nucleus body is asymmetrical in the sagittal plane, the maximum height axis offset from the geometric center axis of the nucleus body and the first planar portion non-parallel with the second planar portion, wherein the planar portions of the nucleus body maintain a fixed angle of correction; and
wherein the nucleus body is composed of a non-resilient material chosen from the group consisting of: polyurethane, polymer, polyethylene, ultra-high molecular weight polyethylene, ceramic, metal, metal alloy, titanium, titanium alloy, chrome-cobalt-molybdenum, cobalt 28 chromium molybdenum, cobalt chrome, and stainless steel.

13. The nucleus of claim 12, wherein the first and second bearing surfaces are separated from one another by a circumferential wall.

14. The nucleus of claim 13, wherein the maximum height axis is perpendicular to the circumferential wall.

15. The nucleus of claim 12, wherein the second bearing surface comprises a second curved portion, the second planar portion formed on the second curved portion.

16. The nucleus of claim 12, wherein at least one of the first and second planar portions is sloped with respect to the circumferential wall to provide the angle of correction.

17. The nucleus of claim 16, wherein the angle of correction is between 3 and 6 degrees.

18. The nucleus of claim 12, wherein the maximum height axis is offset toward an anterior end of the nucleus body to provide a lordotic correction when the nucleus body is properly positioned between first and second end plates attached to adjacent vertebrae.

19. The nucleus of claim 12 and further including first and second end plates adapted to be attached to adjacent vertebrae, the nucleus body being positioned between the end plates to form a total disc replacement.

20. A nucleus for an artificial disc for replacing the natural disc of a human spine and being adapted to fit between and move relative to first and second end plates that are attached to adjacent vertebrae, the nucleus comprising:
a nucleus body having a superior bearing surface and an inferior bearing surface opposite the superior bearing surface, the superior and inferior bearing surfaces on opposite sides of a circumferential wall, the superior and inferior bearing surfaces shaped to engage and rotationally articulate relative to cooperating bearing surfaces formed on the first and second end plates;
the superior bearing surface having a first planar portion positioned between first and second curved portions of the superior bearing surface, the first planar portion extending along the sagittal plane and the first and second curved portions convexly curved in the sagittal plane, wherein the first planar portion is sloped with respect to the circumferential wall, and is configured to extend across the intersection of the coronal and the sagittal planes to provide an angle of correction, the coronal and the sagittal planes defined relative to the nucleus body such that the intersection defines a vertically extending geometric center axis of the nucleus body;
the inferior bearing surface having a second planar portion positioned between third and fourth curved portions of the inferior bearing surface; and
wherein the angle of correction remains constant irrespective of any compressive load on the nucleus.

21. The nucleus of claim 20, wherein first planar portion has an anterior end and a posterior end, wherein the height of anterior end is greater than the height of the posterior end to provide a lordotic correction.

22. The nucleus of claim 20, wherein first planar portion has an anterior end and a posterior end, wherein the height of anterior end is lower than the height of the posterior end to provide a kyphotic correction.

23. The nucleus of claim 20, wherein the second planar portion is non-parallel with the first planar portion.

24. The nucleus of claim 20, wherein the angle of correction is chosen from the group consisting of 3 and 6 degrees.

25. The nucleus of claim 20, and further including first and second end plates adapted to be attached to adjacent vertebrae, the nucleus body being positioned between the end plates to form a total disc replacement.

26. The nucleus of claim 1, wherein the correction orientation of the at least one end plate relative to the nucleus provides a lordotic correction.

27. The nucleus of claim 20, wherein the nucleus body is composed of a non-resilient material chosen from the group consisting of: polyurethane, polymer, polyethylene, ultra-high molecular weight polyethylene, ceramic, metal, metal alloy, titanium, titanium alloy, chrome-cobalt-molybdenum, cobalt 28 chromium molybdenum, cobalt chrome, or stainless steel.

28. The nucleus of claim 19, wherein the planar portions of the nucleus body maintain the fixed angle of correction of the first and second endplates relative to the nucleus body irrespective of any compressive load between the first endplate and the second endplate.

29. The nucleus of claim 25, wherein the angle of correction remains constant irrespective of any compression of the nucleus between the first and second endplates.

30. The nucleus of claim 20, wherein the circumferential wall is located on a radially projecting flange positioned between the inferior and superior bearing surfaces.

\* \* \* \* \*